(12) United States Patent
Goldsby et al.

(10) Patent No.: US 7,820,878 B2
(45) Date of Patent: Oct. 26, 2010

(54) PRODUCTION OF UNGULATES, PREFERABLY BOVINES THAT PRODUCE HUMAN IMMUNOGLOBULINS

(75) Inventors: Richard A. Goldsby, Leverett, MA (US); James M. Robl, Brandon, SD (US); Barbara A. Osborne, Leverett, MA (US); Yoshimi Kuroiwa, Sioux Falls, SD (US)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 93 days.

(21) Appl. No.: 12/151,181

(22) Filed: May 5, 2008

(65) Prior Publication Data

US 2009/0276866 A1 Nov. 5, 2009

Related U.S. Application Data

(63) Continuation-in-part of application No. 11/011,711, filed on Dec. 14, 2004, now abandoned, which is a continuation of application No. 09/714,185, filed on Nov. 17, 2000, now abandoned.

(60) Provisional application No. 60/166,410, filed on Nov. 19, 1999.

(51) Int. Cl.
C12N 15/00 (2006.01)
A01K 67/027 (2006.01)

(52) U.S. Cl. .......................................... 800/24; 800/15

(58) Field of Classification Search .................... 800/24
See application file for complete search history.

(56) References Cited

U.S. PATENT DOCUMENTS

| | | | |
|---|---|---|---|
| 4,797,356 A | 1/1989 | Brandt et al. |
| 4,847,081 A | 7/1989 | Rice |
| 4,873,316 A | 10/1989 | Meade et al. |
| 4,959,317 A | 9/1990 | Sauer |
| 4,994,384 A | 2/1991 | Prather et al. |
| 5,021,244 A | 6/1991 | Spaulding |
| 5,057,420 A | 10/1991 | Massey |
| 5,096,822 A | 3/1992 | Rosenkrans, Jr. et al. |
| 5,160,312 A | 11/1992 | Voelkel |
| 5,175,384 A | 12/1992 | Krimpenfort et al. |
| 5,213,979 A | 5/1993 | First et al. |
| 5,320,952 A | 6/1994 | Deutch et al. |
| 5,346,990 A | 9/1994 | Spaulding |
| 5,374,544 A | 12/1994 | Schwartz et al. |
| 5,434,066 A | 7/1995 | Bebee et al. |
| 5,434,340 A | 7/1995 | Krimpenfort et al. |
| 5,453,366 A | 9/1995 | Sims et al. |
| 5,464,764 A | 11/1995 | Capecchi et al. |
| 5,470,560 A | 11/1995 | Martin, Jr. |
| 5,482,856 A | 1/1996 | Fell, Jr. et al. |
| 5,487,992 A | 1/1996 | Capecchi et al. |
| 5,496,720 A | 3/1996 | Susko-Parrish et al. |
| 5,527,674 A | 6/1996 | Guerra et al. |
| 5,545,806 A | 8/1996 | Lonberg et al. |
| 5,545,807 A | 8/1996 | Surani et al. |
| 5,565,350 A | 10/1996 | Kmiec |
| 5,565,362 A | 10/1996 | Rosen |
| 5,569,825 A | 10/1996 | Lonberg et al. |
| 5,583,016 A | 12/1996 | Villeponteau et al. |
| 5,591,669 A | 1/1997 | Krimpenfort et al. |
| 5,612,205 A | 3/1997 | Kay et al. |
| 5,614,396 A | 3/1997 | Bradley et al. |
| 5,618,686 A | 4/1997 | Kojima et al. |
| 5,625,126 A | 4/1997 | Lonberg et al. |
| 5,627,059 A | 5/1997 | Capecchi et al. |
| 5,631,153 A | 5/1997 | Capecchi et al. |
| 5,633,076 A | 5/1997 | DeBoer et al. |
| 5,633,425 A | 5/1997 | Lonberg et al. |
| 5,639,457 A | 6/1997 | Brem et al. |

(Continued)

FOREIGN PATENT DOCUMENTS

EP 0773288 5/1997

(Continued)

OTHER PUBLICATIONS

Meirelles et al. Complete Replacement of the Mitochondrial Genotype in a Bos indicus Calf Reconstructed by Nuclear Transfer to a Bos taurus Oocyte. Genetics 2001, vol. 158, pp. 351-356.*

(Continued)

*Primary Examiner*—Valarie Bertoglio
(74) *Attorney, Agent, or Firm*—Clark & Elbing LLP

(57) ABSTRACT

The present invention relates to a method of producing an ungulate having both copies of the IgM heavy chain (mu) rag-1 and/or rag-2 gene eliminated from its genome. Animals which have IgM, rag-1 and/or rag-2 eliminated from their genome are unable to conduct the gene rearrangements that are necessary to generate the antigen receptors of B- or T-lymphocytes, and therefore will not develop native B- or T-cells. Because they are unable to produce B- and T-lymphocytes, these IgM, rag-1, or rag-2 ungulates cannot reject human hematopoietic stem cell preparations, and B- and T-lymphocytes which develop therefrom. Therefore, the present invention also involves injecting into IgM, rag-1, and/or rag-2 deficient ungulates, in utero or shortly after birth, human B- and T-lymphocytes whose immune systems produce human immunoglobulin that can be processed for therapeutic uses in humans.

9 Claims, 6 Drawing Sheets

U.S. PATENT DOCUMENTS

| | | |
|---|---|---|
| 5,652,373 A | 7/1997 | Reisner |
| 5,654,182 A | 8/1997 | Wahl et al. |
| 5,660,997 A | 8/1997 | Spaulding |
| 5,661,016 A | 8/1997 | Lonberg et al. |
| 5,677,177 A | 10/1997 | Wahl et al. |
| 5,679,523 A | 10/1997 | Li et al. |
| 5,695,977 A | 12/1997 | Jurka |
| 5,698,763 A | 12/1997 | Weissmann et al. |
| 5,721,367 A | 2/1998 | Kay et al. |
| 5,733,730 A | 3/1998 | De Lange |
| 5,741,957 A | 4/1998 | Deboer et al. |
| 5,750,172 A | 5/1998 | Meade et al. |
| 5,756,325 A | 5/1998 | Kmiec |
| 5,763,240 A | 6/1998 | Zarling et al. |
| 5,770,422 A | 6/1998 | Collins |
| 5,770,429 A | 6/1998 | Lonberg et al. |
| 5,776,744 A | 7/1998 | Glazer et al. |
| 5,780,009 A | 7/1998 | Karatzas et al. |
| 5,780,296 A | 7/1998 | Holloman et al. |
| 5,789,215 A | 8/1998 | Berns et al. |
| 5,789,650 A | 8/1998 | Lonberg et al. |
| 5,789,655 A | 8/1998 | Prusiner et al. |
| 5,801,030 A | 9/1998 | McVey et al. |
| 5,814,318 A | 9/1998 | Lonberg et al. |
| 5,821,117 A | 10/1998 | Sandrin et al. |
| 5,827,690 A | 10/1998 | Meade et al. |
| 5,830,698 A | 11/1998 | Reff et al. |
| 5,837,857 A | 11/1998 | Villeponteau et al. |
| 5,843,643 A | 12/1998 | Ratner |
| 5,843,754 A | 12/1998 | Susko-Parrish et al. |
| 5,849,991 A | 12/1998 | d'Apice et al. |
| 5,849,992 A | 12/1998 | Meade et al. |
| 5,874,299 A | 2/1999 | Lonberg et al. |
| 5,876,979 A | 3/1999 | Andrews et al. |
| 5,877,397 A | 3/1999 | Lonberg et al. |
| 5,891,698 A | 4/1999 | Prieto et al. |
| 5,945,577 A | 8/1999 | Stice et al. |
| 5,952,222 A | 9/1999 | Rosenkrans, Jr. et al. |
| 6,011,197 A | 1/2000 | Strelchenko et al. |
| 6,023,010 A | 2/2000 | Krimpenfort et al. |
| 6,030,833 A | 2/2000 | Seebach et al. |
| 6,054,632 A | 4/2000 | Reid |
| 6,066,719 A | 5/2000 | Zapata |
| 6,074,853 A | 6/2000 | Pati et al. |
| 6,077,710 A | 6/2000 | Susko-Parrish et al. |
| 6,091,001 A | 7/2000 | Jakobovits et al. |
| 6,133,503 A | 10/2000 | Scheffler |
| 6,147,276 A | 11/2000 | Campbell et al. |
| 6,153,428 A | 11/2000 | Gustafsson et al. |
| 6,166,288 A | 12/2000 | Diamond et al. |
| 6,183,993 B1 | 2/2001 | Boyce et al. |
| 6,194,202 B1 | 2/2001 | Susko-Parrish et al. |
| 6,204,061 B1 | 3/2001 | Capecchi et al. |
| 6,204,431 B1 | 3/2001 | Prieto et al. |
| 6,252,133 B1 | 6/2001 | Campbell et al. |
| 6,258,998 B1 | 7/2001 | Damiani et al. |
| 6,271,436 B1 | 8/2001 | Piedrahita et al. |
| 6,300,129 B1 | 10/2001 | Lonberg et al. |
| 6,395,958 B1 | 5/2002 | Strelchenko et al. |
| 6,753,457 B2 | 6/2004 | Wangh et al. |
| 7,074,983 B2 | 7/2006 | Robl |
| 2002/0001842 A1 | 1/2002 | Chapman |
| 2002/0012660 A1 | 1/2002 | Colman et al. |
| 2002/0069423 A1 | 6/2002 | Good et al. |
| 2002/0108132 A1 | 8/2002 | Rapp |
| 2002/0194635 A1 | 12/2002 | Dunne et al. |
| 2004/0068760 A1 | 4/2004 | Robl et al. |
| 2005/0097627 A1 | 5/2005 | Robl |
| 2006/0041945 A1 | 2/2006 | Robl et al. |
| 2006/0117394 A1 | 6/2006 | Robl et al. |
| 2006/0117395 A1 | 6/2006 | Robl et al. |

FOREIGN PATENT DOCUMENTS

| | | |
|---|---|---|
| EP | 0546073 | 9/1997 |
| EP | 0843961 | 5/1998 |
| EP | 1106061 | 6/2001 |
| WO | WO 92/03918 | 3/1992 |
| WO | WO 93/10227 | 5/1993 |
| WO | WO 94/02602 | 2/1994 |
| WO | WO 95/23868 | 9/1995 |
| WO | WO 95/33828 | 12/1995 |
| WO | WO 96/33735 | 10/1996 |
| WO | WO 97/07668 | 3/1997 |
| WO | WO 97/07669 | 3/1997 |
| WO | WO 97/07671 | 3/1997 |
| WO | WO 97/13852 | 4/1997 |
| WO | WO 98/14593 | 4/1998 |
| WO | WO 98/24884 | 6/1998 |
| WO | WO 98/24893 | 6/1998 |
| WO | WO 98/30683 | 7/1998 |
| WO | WO 98/37183 | 8/1998 |
| WO | WO 98/39416 | 9/1998 |
| WO | WO 99/21415 | 5/1999 |
| WO | WO 99/60108 | 11/1999 |
| WO | WO 00/10383 | 3/2000 |
| WO | WO 00/42174 | 7/2000 |
| WO | WO 00/46251 | 8/2000 |
| WO | WO 00/51424 | 9/2000 |
| WO | WO 00/67568 | 11/2000 |
| WO | WO 00/67569 | 11/2000 |
| WO | WO 00/74477 | 12/2000 |
| WO | WO 01/23541 | 4/2001 |
| WO | WO 01/30992 | 5/2001 |
| WO | WO 01/35735 | 5/2001 |
| WO | WO 01/73107 | 10/2001 |
| WO | WO 02/12437 | 2/2002 |
| WO | WO 02/051997 | 7/2002 |
| WO | WO 02/070648 | 9/2002 |
| WO | WO 02/079416 | 10/2002 |
| WO | WO 2004/044156 | 5/2004 |

OTHER PUBLICATIONS

Fehilly et al. Cytogenetic and Blood Group Studies of Sheep/Goat Chimaeras. J. Reproduct. Fertility. 1985, vol. 74, pp. 215-221.*

Denning et al., "Gene Targeting in Primary Fetal Fibroblasts from Sheep and Pig," Cloning and Stem Cells 3:221-231 (2001).

Ehrenstein et al., "Targeted Gene Disruption reveals a Role for Natural Secretory IgM in the Maturation of the Primary Immune Response," Proc. Natl. Acad. Sci., USA 95:10089-10093 (1998).

Erlandsson et al., "Mice with an Inactivated joining chain Locus Have Perturbed IgM Secretion," Eur. J. lmmunol. 28:2355-2365 (1998).

Goldman et al., "Enhanced Human Cell Engraftment in Mice Deficient in RAG2 and the Common Cytokine Receptor Gamma Chain," Br. J. Haematol. 103:335-342 (1998).

Griffiths et al., "Current Concepts of PLP and Its Role in the Nervous System," Microscopy Research and Technique 41:344-358 (1998).

Guidos et al., "Development of CD4+CD8+ Thymocytes in RAG-Deficient Mice Through a T Cell Receptor β Chain-Independent Pathway," J. Exp. Med. 181:1187-1195 (1995).

Ishida et al., "Production of a Diverse Repertoire of Human Antibodies in Genetically Engineered Mice," Microbiol. Immunol. 42:143-150 (1998).

Jonak et al., "Manipulation of Human B Cells to Confer Immortality," Hum. Antibodies Hybridomonas 3:177-185 (1992).

Joziasse et al., "Bovine Alpha 1→3-Galactosyltransferase: Isolation and Characterization of a cDNA Clone. Identification of Homologous Sequences in Human Genomic DNA," J. Biol. Chem. 264:14290-14297 (1989).

Joziasse et al., "Characterization of an α1→3-Galactosyltransferase Homologue on Human Chromosome 12 That Is organized As A Processed Pseudogene," J. Biol. Chem. 266:6991-6998 (1991).

Kaushik et al., "Novel Insight into Antibody Diversification from Cattle," Veterinary Immunology and Immunopathology 87:347-350 (2002).

Kitamura et al., "A B Cell-Deficient Mouse by Targeted Disruption of the Membrane Exon of the Immunoglobulin Mu Chain Gene," Nature 350:423-426 (1991).

Knight et al., "Genetic Engineering of Bovine Ig. Construction and Characterization of Hapten-Binding Bovine/Murine Chimeric IgE, IgA, IgG1, IgG2, and IgG3 Molecules," J. Immunol. 140:3654-3659 (1988).

Kuroiwa et al., "Manipulation of Human Minichromosomes to Carry Greater Than Megabase-Sized Chromosome Inserts," Nat. Biotechnol. 18:1086-1090 (2000).

Lansford et al., "Ig Heavy Chain Class Switching in Rag-Deficient Mice," Int. Immunol. 10:325-332 (1998).

Leonard et al., "Role of the Common Cytokine Receptor γ Chain in Cytokine Signaling and Lymphoid Development," Immunological Reviews 148:97-114 (1995).

Lohka et al., "Formation in Vitro of Sperm Pronuclei and Mitotic Chromosomes Induced By Amphibian Ooplasmic Components," Science 220:719-721 (1983).

Lohka et al., "Induction of Nuclear Envelope Breakdown, Chromosome Condensation And Spindle Formation in Cell-Free Extracts," J. Cell Biol. 101:518-523 (1985).

Loupart et al., "Differential Stability of a Human Mini-Chromosome in Mouse Cell Lines," Chromosoma 107:255-259 (1998).

Martin et al., "Engraftment of Human Lymphocytes and Thyroid Tissue into Scid and Rag2-Deficient Mice: Absent Progression of Lymphocytic Infiltration," J. Clin. Endocrinol. Metab. 79:716-723 (1994).

Mazurier et al., "A Novel Immunodeficient Mouse Model—Rag2 x Common Cytokine Receptor Gamma Chain Double Mutants—Requiring Exogenous Cytokine Administration for Human Hematopoietic Stem Cell Engraftment," J. Interferon cytokine Res. 19:533-541 (1999).

Miake-Lye et al., "Induction of Early Mitotic Events in a Cell-Free System," Cell 41:165-175 (1985).

Mocikat, "Improving the Expression of Chimeric Antibodies Following Homologous Recombination in Hybridoma Cells," J. Immunol. Methods 225:185-189 (1999).

Moens et al., "Defects tin Heart and Lung Development in Compound Heterozygotes for Two Different Targeted Mutations at the N-myc Locus," Development 119:485-499 (1993).

Newport, "Nuclear Reconstitution in Vitro: Stages of Assembly Around Protein-Free DNA," Cell 48:205-217 (1987).

Parng et al., "Gene Conversion Contributes to Lg Light Chain Diversity in Cattle," J. of Immun. 157:5478-5486 (1996).

Polejaeva et al., "New Advances in Somatic Cell Nuclear Transfer: Application in Transgenesis," Theriogenology 53:117-126 (2000).

Rideout et al., "Nuclear Cloning and Epigenetic Reprogramming of the Genome," Science 293:1093-1098 (2001).

Schnieke et al., "Human Factor IX Transgenic Sheep Produced by Transfer of Nuclei From Transfected Fetal Fibroblasts," Science 278:2130-2133 (1997).

Shen et al., "Human Mini-Chromosomes in Mouse Embryonal Stem Cells," Hum. Mol. Genet. 6:1375-1382 (1997).

Srikumaran et al., "Bovine X Mouse Hybridomas that Secrete Bovine Immunoglobulin G1," Science 220:522-524 (1983).

Steen et al., "A Kinase-Anchoring Protein (AKAP)95 Recruits Human Chromosome-Associated Protein (hCAP)-D2/Eg7 for Chromosome Condensation in Mitotic Extract," J. Cell Biol. 149:531-536 (2000).

Steen et al., "Recruitment of Protein Phosphatase 1 to the Nuclear Envelope By A Kinase-Anchoring Protein AKAP149 Is A Pre-Requisite for Nuclear Lamina Assembly," J. Cell Biol.150:1251-1261 (2000).

Suprynowicz et al., "A Fractionated Cell-Free System for Analysis of Prophase Nuclear Disassembly," J. Cell Biol. 103:2073-2081 (1986).

Tomizuka et al., "Double Trans-Chromosomic Mice: Maintenance of Two Individual Human Chromosome Fragments Containing Ig Heavy and Kappa Loci and Expression of Fully Human antibodies," Proc. Natl. Acad. Sci, USA 97:722-727 (2000).

Wilson et al., "A Trypsin-Sensitive Receptor On Membrane Vesicles Is Required for Nuclear Envelope Formation in Vitro," J. Cell Biol. 107:57-68 (1988).

Yahata et al., "Reconstitution of Immune Systems in RAG2 −/− Mice by Transfer with Interleukin-12-Induced Splenic Hematopoietic Progenitor Cells," Immunol. Lett. 62:165-170 (1998).

Echelard et al., "Toward a New Cash Cow: Cloned cattle engineered to carry an artificial chromosome encoding human immunoglobulin genes are a significant leap toward the production of safer and more potent therapeutic antibodies," Nat. Biotechnol. 20:881-882 (2002).

Farrugia et al., "Intravenous immunoglobulin: regulatory perspectives on use and supply," Trans. Med. 11:63-74 (2001).

Fishwild et al., "High-avidity human IgGk monoclonal antibodies from a novel strain of minilocus transgenic mice," Nat. Biotech. 14:845-851 (1996).

Ishida et al., "Production of human monoclonal and polyclonal antibodies in transchromo animals," Clon. Stem Cells. 4:91-102 (2002).

Joziasse et al., "Xenotransplantation: the importance of the Galα 1,3Gal epitope in hyperacute vascular rejection," Biochim. Et BioPhys Acta. 1455:403-418 (1999).

Kuroiwa et al., "Cloned transchromosomic calves producing human immunoglobulin," Nat. Biotech. 20:889-894 (2002).

Lonberg et al., "Human antibodies from transgenic mice," Intern. Rev. Immun. 13:65-93, (1995).

Lucier et al., "Multiple sites of Vλ diversification in cattle," J. Immun. 161:5438-5444 (1998).

Mendez et al., "Functional transplant of megabase human immunoglobulin loci recapitulates human antibody response in mice," Nat. Genet.I 15:146-156 (1997).

Raeber et al., "Ectopic expression of prion protein (PrP) in T lymphocytes or hepatocytes of PrP knockout mice is insufficient to sustain prion replication," Proc. Natl. Acad. Sci. 96:3987-3992 (1999).

Sandrin et al., "Recent advances in xenotransplantation," Curr. Opin. In Immun. 11:527-531 (1999).

Stiehm et al., "Appropriate therapeutic use of immunoglobulin," Trans. Med. Rev. X:203-221 (1996).

Tomizuka et al., "Functional expression and germline transmission of a human chromosome fragment in chimaeric mice," Nat. Genet. 16:133-143 (1997).

Baguisi et al., "Production of Goats by Somatic Cell Nuclear Transfer," Nature Biotechnology. 17:456-461 (1999).

Co et al., "Generation of Transgenic Mice and Germline Transmission of a Mammalian Artificial Chromosome Introduced into Embryos by Pronuclear Microinjection," Chromosome Research. 8:183-191 (2000).

Eyestone et al., "Nuclear Transfer from Somatic Cells: Applications in Farm Animal Species," Journal of Reproduction and Fertility Supplement. 54:489-497 (1999).

Grimes et al., "Engineering Mammalian Chromosomes," Human Molecular Genetics. 7:1635-1640 (1998).

Langford et al., "Production of Pigs Transgenic for Human Regulators of Complement Activation Using YAC Technology," Transplantation Proceedings. 28:862-863 (1996).

Niemann et al., "Transgenic Livestock: Premises and Promises," Animal Reproduction Science. 60-61:277-293 (2000).

Prather et al., "Development of the Techniques for Nuclear Transfer in Pigs," Theriogenology. 51: 487-498 (1999).

Sun et al., "Expressed Swine $V_H$ Genes Belong to a Small $V_H$ Gene Family Homologous to Human $V_H$III," The Journal of Immunology. 153:618-5627 (1994).

Zhao et al., "Artiodactyl IgD: The Missing Link," The Journal of Immunology. 169:4408-4416 (2002).

Zuelke, "Transgenic Modification of Cows Milk for Value-Added Processing," Reproduction, Fertility Development. 10:671-676 (1998).

Clark et al., "A future for Transgenic livestock," Nature Reviews Genetics. 4:825-833 (2003).

Niemann et al., "Transgenic Farm animals: Present and Future," Rev. Scht Tech. Off Int. Spiz. 24:285-298 (2005).

Wheeler et al., "Transgenic Technology and Applications in Swine," Theriogenology. 56:1345-1369 (2001).

Prelle et al., "Pluripotent Stem Cells-Models of Embryonic Development, Tool for Gene Targeting, and Basis of Cell Therapy," *Anat. Histol. Embryol.* 31:169-186 (2002).

Pennisi et al., "Clones: A Hard Act to Follow," *Science* 288:1722-1727 (2000).

Campbell, "Nuclear Transfer in Farm Animal Species," *Seminars in Cell & Develop. Biol.* 10:245-252 (1999).

Weissman, "Molecular Biology of Transmissible Spongiform Encephalopathies," *FEBS Letters*. 389:3-11 (1996).

Hamers-Casterman et al., "Naturally Occurring Antibodies Devoid of Light Chains," *Nature*. 363:446-448 (1993).

Bosch et al., "Isolation, Characterization, Gene Modification, and Nuclear Reprogramming of Porcine Mesenchymal Stem Cells," *Biology of Reproduction*. 74:46-57 (2006).

Dai et al., "Targeted Disruption of the $\alpha$1,3-Galactosyltransferase Gene in Cloned Pigs," *Nature Biotechnology*. 20:251-255 (2002).

Hyun et al., "Production of Nuclear Transfer-Derived Piglets Using Porcine Fetal Fibroblasts Transfected with the Enhanced Green Fluorescent Protein," *Biology of Reproduction*. 69:1060-1068 (2003).

Lai et al., "Production of $\alpha$1,3-Galactosyltransferase Knockout Pigs by Nuclear Transfer Cloning," *Science*. 295:1089-1092 (2002).

Lai et al., "Creating Genetically Modified Pigs by Using Nuclear Transfer," *Reproductive Biology and Endocrinology*. 1:82 (2003).

Keefer et al., "Generation of Dwarf Goat (*Capra hircus*) Clones Following Nuclear Transfer with Transfected and Nontransfected Fetal Fibroblasts and in Vitro-Matured Oocytes," *Biology of Reproduction*. 64:849-856 (2001).

Martinez Diaz et al., "Effect of Fusion/Activation Protocol on in Vitro Development of Porcine Nuclear Transfer Embryos Constructed with Foreign Gene Transfected Fetal Fibroblasts," *J. Vet. Med. Sci.* 65:989-994 (2003).

Park et al., "Developmental Potential of Porcine Nuclear Transfer Embryos Derived From Transgenic Fetal Fibroblasts Infected with the Gene for the Green Fluorescent Protein: Comparison of Different Fusion/Activation Conditions," *Biology of Reproduction*. 65:1681-1685 (2001).

Prather et al., "Nuclear Remodeling and Reprogramming in Transgenic Pig Production," *Exp. Biol. Med*. 229:1120-1126 (2004).

Ramsoondar et al., "Production of $\alpha$1,3-Galactosyltransferase-Knockout Cloned Pigs Expressing Human $\alpha$1,2-Fucosylosyltransferase," *Biology of Reproduction*. 69:437-445 (2003).

Watanabe et al., "A Novel Method for the Production of Transgenic Cloned Pigs: Electroporation-Mediated Gene Transfer to Non-cultured Cells and Subsequent Selection with Puromycin," *Biology of Reproduction*. 72:309-315 (2005).

Leno et al., "Initiation of DNA Replication in Nuclei from Quiescent Cells Requires Permeabilization of the Nuclear Membrane," The Journal of Cell Biology 127:5-14 (1994).

Yang, "Application of Xenogeneic Stem Cells for Induction of Transplantation Tolerance: Present State and Future Directions," *Springer Semin. Immun*. 26:187-200 (2004).

Greiner et al., "SCID Mouse Models of Human Stem Cell Engraftment," *Stem Cell* 16:166-177 (1998).

Clark et al., "Gene targeting in livestock: a preview," *Transgenic Research*. 9:263-275 (2000).

Ahearn et al., "Disruption of the *Cr2* Locus Results in a Reduction in B-1a Cells and in an Impaired B Cell Response to T-Dependent Antigen," *Immunity* 4:251-262 (1996).

Burke et al., "A Cell Free System to Study Reassembly of the Nuclear Envelope at the End of Mitosis," Cell 44:639-652 (1986).

Cibelli et al., "Bovine Chimeric Offspring Produced By Transgenic Embryonic Stem Cells Generated From Somatic Cell Nuclear Transfer Embryos," Theriogenology p. 236, vol. 49, 1998.

Cibelli et al., "Cloned Transgenic Calves Produced from Nonquiescent Fetal Fibroblasts," Science 280:1256-1258 (1998).

Collas et al., "Lipophilic Organizing Structures of Sperm Nuclei Target Membrane Vesicle Binding and Are Incorporated Into the Nuclear Envelope," Dev. Biol. 169:123-135 (1995).

Collas, "Sequential PKC- and Cdc2-Mediated Phosphorylation Events Elicit Zebrafish Nuclear Envelope Disassembly," J. Cell Sci. 112:977-987 (1999).

Collas et al., "The A-Kinase-Anchoring Protein, AKAP95, Is A Multivalent Protein With A Key Role In Chromatin Condensation At Mitosis," J. Cell Biol. 147:1167-1179 (1999).

Cubizolles et al., "pEg7, A New Xenopus Protein Required For Mitotic Chromosome Condensation in Egg Extracts," J. Cell Biol. 143:1437-1446 (1998).

Denning et al., "Deletion of the $\alpha(1,3)$Galactosyl Transferase (GGTA1) Gene and the Prion Protein (PrP) Gene in Sheep," Nat. Biotechnol. 19:559-562 (2001).

\* cited by examiner

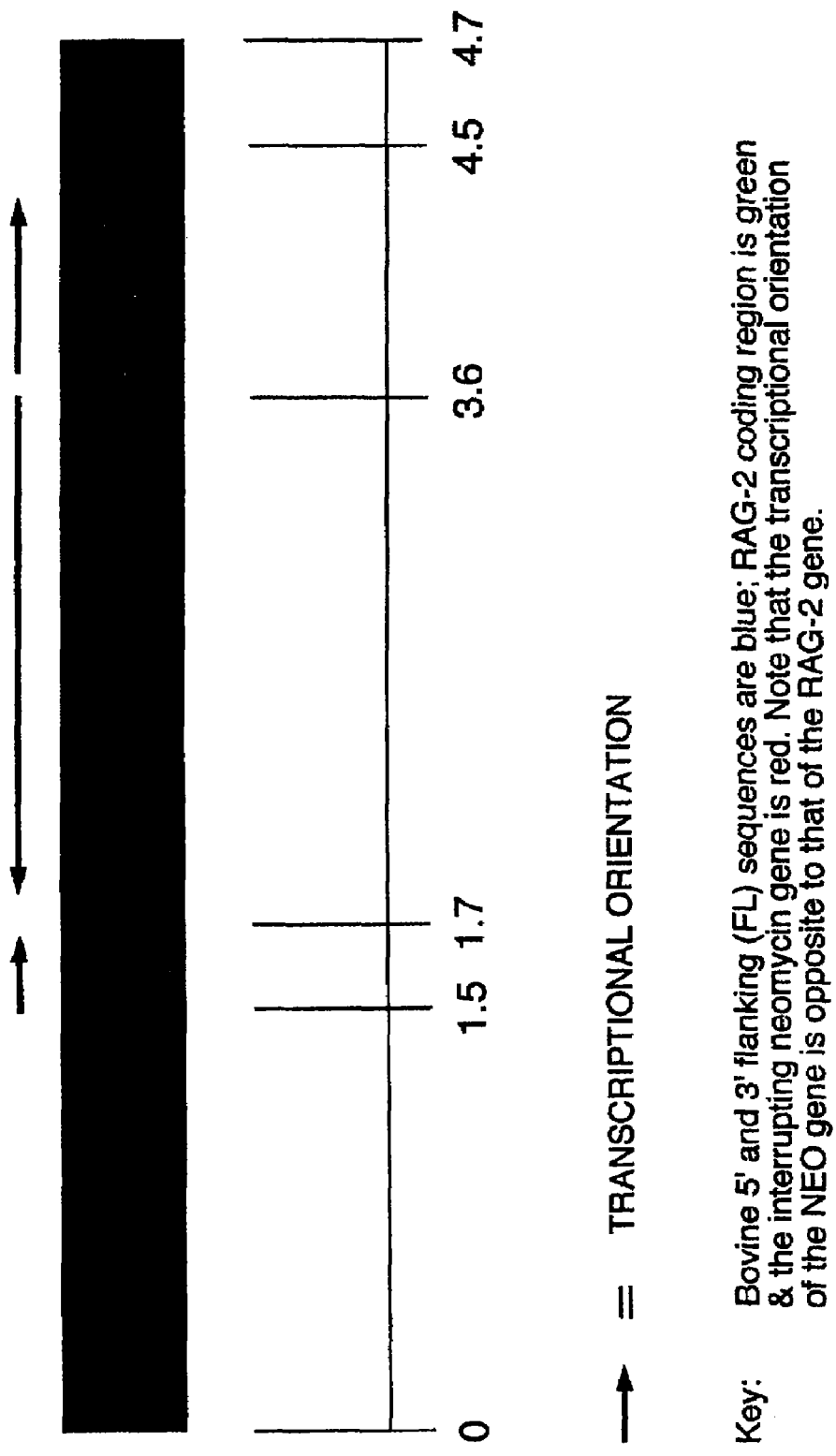
FIG. 1 MAP OF BOVINE RAG-2 KNOCKOUT CONSTRUCT

FIG. 2 (PG 1 OF 2)

BOVINE RAG2 SEQUENCE

```
>
>
>    773 ATGTCACT ACAGATGGTA ACAGTCGGAA
>
>    801 ATAGCATAGC CTTAATTCAA CCAGGCTTCT CGTTAATGAA
TTTTGATGGG
>
>    851 CAAGTTTTCT TCTTTGGCCA AAAAGGCTGG CCCAAGAGGT
CTTGCCCCAC
>
>    901 TGGAGTTTTC CATTTTGAGG TAAAGCATAA TCATCTTAAA
CTGAAGCCTG
>
>    951 CAGTTTTCTC TAAGGATTCC TGCTACCTTC CTCCTCTTCG ATACCGGGC
>
>   1001 CACTTGCACA TTCAGCGGCC AACTTGGAGT CTGAAAAGCA
TCAGTACATC
>
>   1051 ATCCATGGAG GAAAAACACC AAACAATGAG CTTTCAGATA
AGATTTATGT
>
>   1101 GATGTCTGTT GTTTCCAAGA ACAACAAAAA AGTTACCTTT
CGCTGCACAG
>
>   1151 AGAAGGACTT GGTAGGAGAC ATTCCTGAAG GCAGATATGG
TCATTCCATT
>
>   1201 GATGTGGTGT ATAGTCGGGG GAAAAGTATG GGTGTTCTCT
TTGGAGGACG
>
>   1251 GTCATACATA CCTTCTGCCC AAAGAACCAC AGAGAAATGG
AACAGTGTAG
>
>   1301 CTGACTGCCT GCCCCATGTC TTCTTGGTGG ATTTTGAATT
TGGGTGCTCT
>
>   1351 ACGTCATACA TTCTTCCAGA ACTTCAAGAT GGACTATCTT
TTCATGTCTC
>
>   1401 CATTGCCAGA AATGATACCG TTTATATTTT AGGAGGCCAT
TCACTTGCCA
>
>   1451 ATAACATCCG CCCTGCCAAT CTGTACAGAA TAAGGGTTGA
TCTCCCCCTG
>
```

FIG. 2 (PG 2 OF 2)

BOVINE RAG2 SEQUENCE

```
> 1501 GGTAGCCCAG CTGTGGAGTG CACAGTCTTG CCAGGAGGAA
TCTCTGTCTC
>
> 1551 CAGTGCAATC CTGACTCAAA TAAGCAATGA TGAATTTGTT
ATTGTTGGTG
>
> 1601 GCTATCAGCT TGAAAATCAA AAAAGAATGG TCTGTAACAT
CATCTCTTTC
>
> 1651 AAGTATAACA AGATAGACAT TCTTGAGATG GAAACCCCAG
ATTGGACCCC
>
> 1701 AGATATTAAG CACAGCAAGA TATGGTTTGG AAGCAACATG
GGAAATGGAA
>
> 1751 CTGTTTTCCT CGGCATACCA GGAGACAATA AACAGGCTGT
TTCAGAAGCA
>
> 1801 TTTTACTTCT ATACATTGAA ATGTGCTGAA GACGATGTGA
ACGAAGATCA
>
> 1851 GATAACTTTG ACAAGTAGTC AGACATCAAC AGAAGACCCA
GGGGACTCCA
>
> 1901 CTCCCTTTGA AGACTCAGAA GAATTTTGCT TCAGCGCAGA
AGCAAACAGT
>
> 1951 TTCGATGGTG ATGATGAATT TGACACCTAC AATGAAGATG
ATGAGGAAGA
>
> 2001 TGAGTCTGAG ACAGGCTATT GGATTACATG CTGCCCTACT
TGTGATGTGG
>
> 2051 ATATCAATAC GTGGGTACCA TTTTATTCAA CTGAGCTCAA
CAAGCCTGCC
>
> 2101 ATGATCTATT GCTCTCATGG AGATGGACAT TGGGTCCATG
CCCAGTGTAT
>
> 2151 GGATCTGGCA GAACGCACCA CCTCATCCAT CTATCAGAAG
GAAGCAATAA
>
> 2201 ATATTAYTGT AACGAGCATG TGGAGATAG
```

Knockout strategy for bovine *Rag2* gene

The 4.5 Kb region containing the exons encoding the Mu constant region and associated transmembrane domain exons, were deleted and replaced with the loxP-flanked neomycin resistance cassette (Not I fragment)

PRODUCTION OF UNGULATES, PREFERABLY BOVINES THAT PRODUCE HUMAN IMMUNOGLOBULINS

CROSS REFERENCE TO RELATED APPLICATIONS

This application is a continuation-in-part application of U.S. Utility application Ser. No. 11/011,711, filed Dec. 14, 2004, now abandoned, which in turn is a continuation of U.S. Utility application Ser. No. 09/714,185, filed Nov. 17, 2000, now abandoned, which claims benefit of U.S. Provisional Application 60/166,410, filed Nov. 19, 1999.

BACKGROUND OF THE INVENTION

I. Field of the Invention

This invention relates to a method for stably engrafted non-bovine (xenogeneic), preferably human B- and T-cells in ungulates, and other hoofed animals such as bovines, pigs, horses, sheep, buffalo, and goats. The method of the present invention is particularly advantageous because it should result in cloned ungulates and other hoofed animals, e.g., bovines, that produce non-bovine, preferably human in lieu of endogenous antibodies. The invention more specifically relates to a method for producing IgM, Igα, E2A, EBF, BSAP, rag-1, or rag-2 knockout ungulates, that do not express endogenous immunoglobulins, which are engrafted with heterologous hematopoietic stem cells.

II. Description of the Related Art

One of the major impediments facing the development of in vivo therapeutic and diagnostic applications for antibodies in humans is the intrinsic immunogenicity of non-human immunoglobulins. For example, when immunocompetent human patients are administered therapeutic doses of rodent antibodies, the patients produce antibodies against the rodent immunoglobulin sequences; these human anti-mouse antibodies (HAMA) neutralize the therapeutic antibodies and can cause acute toxicity. Hence, it is desirable to produce human immunoglobulins that are reactive with specific antigens that are pathogenic or contribute to pathogenic conditions, or are otherwise promising therapeutic and/or diagnostic targets.

Present technology for obtaining polyclonal human antibody for use in passive immunotherapy or prophylaxis involves collection of blood from thousands of human donors, pooling it, and extracting human immunoglobulin. This technology producing human antibody or use in therapy has two major drawbacks. First, the supplies of human blood are too small to meet the demand for human immunoglobulin. Second, medical and ethical considerations preclude the deliberate immunization of human donors with a broad panel of microbes and other agents, many of which are potentially pathogenic, to assure that antibodies to these agents are present and of the highest practicable titer. There are no improvements to this current technology for obtaining polyclonal human antibody for passive immunotherapy that are likely to solve these important quantitative and qualitative problems.

Previous technology for generating monoclonal antibodies involved pre-exposing, or priming, an animal (usually a rat or mouse) with antigen, harvesting B-cells from that animal, and generating a library of hybridoma clones. By screening a hybridoma population for antigen binding specificity (idiotype) and also screening for immunoglobulin class (isotype), it is possible to select hybridoma clones that secrete the desired antibody. However, when these methods are applied for the purpose of generating human monoclonal antibodies, obtaining hybridomas that produce human antibodies of predefined specificity is a serious technological obstacle.

The construction of animals that are transgenic for various forms, rearranged and unrearranged, of human immunoglobulin genes has been used to produce human antibodies in nonhuman species.

Transgenic animals which produce foreign immunoglobulin are well known in the art. For example, Lonberg et al. (U.S. Pat. Nos. 5,814,318; 5,877,397; 5,874,299; 5,789,650; 5,770,429; 5,661,016; 5,625,126; and 5,545,806) disclose a method of producing transgenic non-human animals which produce human antibodies. The methods of Lonberg et al. involved either suppressing the endogenous immunoglobulin genes by using antisense polynucleotides and/or antiserum directed against endogenous immunoglobulins or inactivating both the endogenous light and heavy chain genes by homologous recombination. They next introduced sequences encoding the foreign immunoglobulin genes thereby producing a transgenic animal. The method of Lonberg et al. produces a variety of antibodies having various isotypes specific for a specific antigen.

Surani et al. (U.S. Pat. No. 5,545,807) also discloses a method for producing antibodies from transgenic animals. The method of Surani et al. involves using a host animal which lacks the genetic material relevant for encoding immunoglobulins. To this animal host, genetic material is added that encodes for heterologous unrearranged and rearranged immunoglobulin heavy and light chain of foreign origin capable of undergoing isotype switching in vivo. Following immunization, polyclonal antisera may be produced from such a transgenic animal. The transgenic non-human animals produced by the method of Surani et al. are able to produce, in one embodiment, IgG, IgA, and/or IgE antibodies that are encoded by human immunoglobulin genetic sequences and which also bind specific human antigens with high affinity.

DeBoer et al. (U.S. Pat. No. 5,633,076) and Meade et al. (U.S. Pat. No. 5,849,992) both disclose the production of transgenic cows which produce antibodies in their milk. DeBoer et al. produce transgenic cows by introducing a transgene, encoding an antibody gene operably linked to a mammary specific promoter, into a cow zygote. Meade et al. produce transgenic mammals which express antibodies in their milk by introducing downstream of a mammary specific promoter foreign DNA segments encoding specific paired immunoglobulin heavy and light chains.

However, the use of transgenics to produce domestic animals that express human antibodies for passive immunotherapy requires the solution of a number of problems. These include the levels at which human antibody transgenes might be expressed in non-human hosts, their ability to undergo class switching, affinity maturation and the immunogenicity in humans of inappropriately glycosylated human antibody. These problems stem from the introduction and expression of human antibody genes in non-human cells. A system that would allow for the introduction of human hematopoietic stem cells into non-humans, especially large animals of agricultural interest such as bovines and other ungulates (e.g., cattle, sheep, or goats), and their development into immunocompetent human B-cells would provide a comprehensive solution of these problems.

However, the immune system poses a major barrier to the introduction of foreign hematopoietic stem cells into an animal of another species. With respect to this barrier, it has been reported that the immune system can potentially be disabled by targeted disruption of rag-1 or rag-2 (recombinase activating gene) (hereinafter rag-1 knockout or rag-2 knockout). (See, e.g., Martin et al., *J. Clin. Endocrinol.* 79(3):716-723

(1994); Mazurier et al., *J Interferon Cytokine Res.* 19(5):533-541 (1999); and Goldman et al., *Br. J. Haematol.* 103(2):335-342 (1998)). Also, the production of IgM knockout mice that do not express functional endogenous B-cells have been reported. (See, Ehrenstein et al., *Proc. Natl. Acad. Sci., USA* 95(17):10089-10093 (1998); and Erlandsson et al., *Eur. J. Immunol.* 28(8):2355-2365 (1998)). Rag-1 or rag-2 knockout animals potentially are unable to conduct the gene rearrangements that are necessary to generate the antigen receptors of B or T lymphocytes. Consequently, they do not develop native B- or T-cells. Moreover, because these animals do not produce B and T lymphocytes, the use of rag-1 or rag-2 knockout mice for engraftment of human hematopoietic stem cells has been reported.

Particularly, such a system has been developed in mice, wherein human hematopoietic progenitor cells have been added to rag-2 knockout mice. Yahata et al., *Immunol. Lett.* 62(3):165-170 (1998) discloses transferring IL-12-induced splenic hematopoietic progenitor cells into rag-2 knockout mice to reconstitute their immune system. This resulted in the production of mice having stably engrafted therein both human B- and T-lymphocytes. However, while the development of human B- and T-lymphocytes in mice has been reported, there has been no report of human or other heterologous species hematopoietic stem cells stably engrafted into an ungulate or any indication that such cells, if stably engrafted will begin to develop into fully immunocompetent B- and T-cells when implanted into ungulates that do not produce B-cells because of a genetic modification, e.g., IgM, Igα, EIA, BSAP, EBF, rag-1, or rag-2 knockout animals other than mice, and more specifically large agricultural animals such as cattle and other ungulates.

While it is anticipated that ungulates will be able to become stably engrafted with human stem cells and provide for the development of xenogeneic immunocompetent B- and T-cells in ungulates and other hoofed animals for which endogenous antibody production has been knocked out, e.g., by knockout of IgM, rag-1, or rag-2 gene, this outcome may not be feasible for various reasons. For example, natural killer cells do not depend on the rearrangement of antigen receptor genes for their cell killing activities. Consequently foreign lymphocytes, e.g., human lymphocytes potentially may be attacked by endogenous natural killer cells and thereby prevent the establishment of human B- and T-cells populations in B-cell deficient ungulates, e.g., IgM, rag-1, or rag-2 deficient animals (provide for stable engraftment). Furthermore, the manner by which B-cells and antibodies develop in humans is quite different from, for example, cattle or other ungulates. In humans, B-cells arise in bone marrow and the primary repertoire is diversified by extensive rearrangement and junctional diversity. By contrast, in cattle, bone marrow is not the site of B-cell origin. Primary repertoire diversification takes place in the spleen and gut associated lymphoid tissue rather than in bone marrow. Also, repertoire diversification in cattle uses relatively few rearrangements and little junctional diversity. Most of the diversity seen in the primary repertoire is the result of massive, variable region focused somatic mutation of rearranged genes. The sharp differences in B-cell development and primary repertoire development between humans and cattle makes it unpredictable whether a functional and diverse repertoire of human B-cells will develop from human hematopoietic stem cells transplanted into cattle and other ungulates and hoofed animals.

Furthermore, until now, various technical barriers have prevented the creation of ungulates, and other large agricultural animals, e.g., cattle, sheep, horses, goats, and buffalo, that have been genetically manipulated in order to knockout antibody production, e.g., by genetically knocking out B-cell production and optionally T-cell production. Particularly, the use of conventional protocols for obtaining double knockouts in primary cell lines with limited life spans in culture is uncertain and difficult. The present inventors propose a method that should overcome these barriers and provides a protocol for producing ungulates having a double knockout that prevents B-cell formation, e.g., E2A, EBF, BSAP, IgM, rag-1, and rag-2 knockout ungulates, especially cattle which have stably engrafted foreign B- and T-lymphocytes, preferably human, canine, feline, rat, or murine, and which produce foreign immunoglobulins in their serum of the species of origin of the particular engrafted hematopoietic stem cells.

SUMMARY OF THE INVENTION

A major object of the present invention is to provide a method for producing a cloned ungulate wherein the expression of both copies of a gene essential for B-cell formation, e.g., Igα, IgM, EIA, EBF, BSAP, rag-1, or rag-2 gene have been eliminated, which said method comprises:

(i) producing an ungulate cell wherein the expression of both copies of a gene which is essential for antibody or B-cell production, e.g., Igα, IgM (mµ) EBF, E2A, BSAP, rag-1, and/or rag-2 gene is eliminated by targeted disruption;

(ii) using said cell or nucleus thereof as a donor cell for nuclear transfer by fusing or inserting such donor cell or nucleus with a suitable recipient cell, e.g., an enucleated oocyte or blastomere and activating the resulting nuclear transfer unit and/or the oocyte prior to or simultaneous to nuclear transfer and culturing in a suitable medium to produce a nuclear transfer embryo;

(iii) introducing said nuclear transfer embryo into a female surrogate; and (iv) obtaining a cloned ungulate that expresses the genotype of the donor differentiated cell, in which expression of both copies of the IgM (mu), Igα, E2A, EBF, BSAP, rag-1, and/or rag-2 gene has been knocked out.

Another object of the invention is to produce ungulates, or other hoofed animals, preferably cattle, wherein endogenous antibody production is knocked out non-genetically, i.e., by the administration of a monoclonal antibody against endogenous IgM which is administered while the animal is in utero, and engrafting heterologous hematopoietic stem cells, preferably human, canine, murine, or feline in utero or shortly after birth.

Still another object of the invention involves the combination of genetic and non-genetic approaches in order to obtain cattle or other ungulates which produce human immunoglobulins or that of other species in their serum by producing an animal that contains and expresses a chromosomal minilocus containing genes necessary for non-ungulate antibody production, e.g., human antibody production, and by administering to such animal while in utero an antibody produced against endogenous bovine antibody so as to ablate B-cells that express endogenous bovine antibodies and selectively retain B-cells that produce non-bovine antibodies.

A further object of the present invention is to provide a method for producing a ungulate cell, preferably bovine wherein the expression of both copies of the Igα, IgM heavy chain (mu) rag-1, rag-2, EBF, E2A, or BSAP gene have been eliminated by targeted disruption, said method comprising the following steps:

(a) contacting a desired ungulate cell, preferably a differentiated cell, with at least one DNA construct which upon interaction with at least one of the Igα, IgM heavy chain gene, rag-1, rag-2, EBF, E2A, or BSAP gene is capable of eliminating the expression by targeted disruption of one copy of said gene;

(b) using said ungulate cell or the nucleus thereof as a nuclear transfer donor to produce a nuclear transfer embryo wherein one or both copies of such gene have been knocked out;

(c) implementing said nuclear transfer embryo into an animal to produce a fetus and obtaining a cell, preferably a differentiated somatic cell is from such embryo, and contacting same with a second DNA construct that eliminates the expression of the second copy of the same gene, i.e., Igα, IgM, rag-1, rag-2, EBF, E2A, or BSAP by homologous recombination;

(d) using the resulting double knockout cell is used as a nuclear transfer donor to produce a second nuclear transfer embryo which is implanted into an ungulate and producing a fetus or offspring wherein both copies of said gene are knocked out and which animal does not produce functional B-cells.

It is a further object of the present invention to provide a method for producing a cloned ungulate wherein the expression of both copies of the Igα, IgM heavy chain, E2A, EBF, BSAP, rag-1, and/or rag-2 genes have been eliminated, wherein said method comprises:

(i) producing an ungulate cell wherein the expression of both copies of the Igα:, IgM heavy chain, rag-1, rag-2, EBF, E2A, or BSAP gene have been eliminated;

(ii) using said cell as a donor cell for nuclear transfer by introducing said cell or DNA derived therefrom into a suitable recipient cell, preferably in metaphase II, and most preferably an enucleated metaphase II oocyte or blastomere;

(iii) fusing said donor cell or nucleus and recipient cell, activating the resulting nuclear transfer unit or recipient cell, during, and/or after fusion, and culturing in a suitable culture medium to produce a nuclear transfer embryo;

(iv) introducing said nuclear transfer embryo into a female surrogate;

(v) obtaining a cloned ungulate that expresses the genotype of the donor cells in wherein both copies of the Igα, IgM heavy chain, rag-1, rag-2, EBF, E2A, or BSAP genes have been eliminated;

(vi) optionally introducing into the cloned ungulate xenogeneic hematopoietic stem cells, preferably human, canine, feline, or murine hematopoietic stem cells.

It is a related object of the invention to collect B-cells from said animal.

It is yet another object of the present invention to isolate polyclonal or monoclonal xenogeneic antibodies from cloned ungulates preferably human, canine, feline, or murine antibodies wherein both copies of the Igα, IgM heavy chain, rag-1, rag-2, EBF, E2A, or BSAP genes have been eliminated.

It is yet another object of the present invention to produce antigen specific polyclonal or monoclonal xenogeneic antibodies, preferably human, canine, feline, or murine by immunization of cloned ungulates wherein both copies of the Igα, IgM heavy chain, rag-1, rag-2, EBF, E2A, or BSAP genes have been eliminated with xenogeneic hematopoietic stem cells of a different species.

It is another object of the invention to provide cloned ungulates wherein both copies of the Igα, IgM, rag-1, rag-2, EBF, E2A, or BSAP gene have been knocked out by:

(1) producing a female ungulate cell wherein one copy of the Igα, IgM, rag-1, rag-2, EBF, E2A, or BSAP has been knocked out by homologous recombination;

(2) producing a male ungulate cell line wherein one copy of the Igα, IgM, rag-1, rag-2, EBF, E2A, or BSAP has been knocked out by homologous recombination;

(3) using a female and male cell produced according to (1) and (2) as a nuclear transfer donors to respectively produce a cloned female and male ungulate, each respectively having one copy of the Igα, IgM, rag-1, rag-2, EBF, E2A, or BSAP gene knocked out;

(4) mating said male and female knockout animals and selecting for progeny wherein both copies of a gene essential for B-cell production have been knocked out by homologous recombination, e.g., the Igα, IgM, rag-1, rag-2, EBF, E2A, or BSAP; and optionally;

(5) introducing xenogeneic, preferably human, canine, feline, or murine hematopoietic stem cells into said cloned ungulate.

BRIEF DESCRIPTION OF THE DRAWINGS

FIG. 1. This figure is a schematic diagram of a targeting construct used for effecting inactivation of the rag-2 gene. In the figure: the organization of the endogenous rag-2 gene is shown with an arrow representing the direction of transcription; the targeting construct maintains the sequences 5' and 3' of the rag-2 coding region; and the coding region is disrupted with a neomycin gene in the opposite transcriptional orientation.

FIG. 2. This figure contains the sequence of the bovine rag-2 gene.

DETAILED DESCRIPTION OF THE PREFERRED EMBODIMENTS OF THE INVENTION

Figure 3:
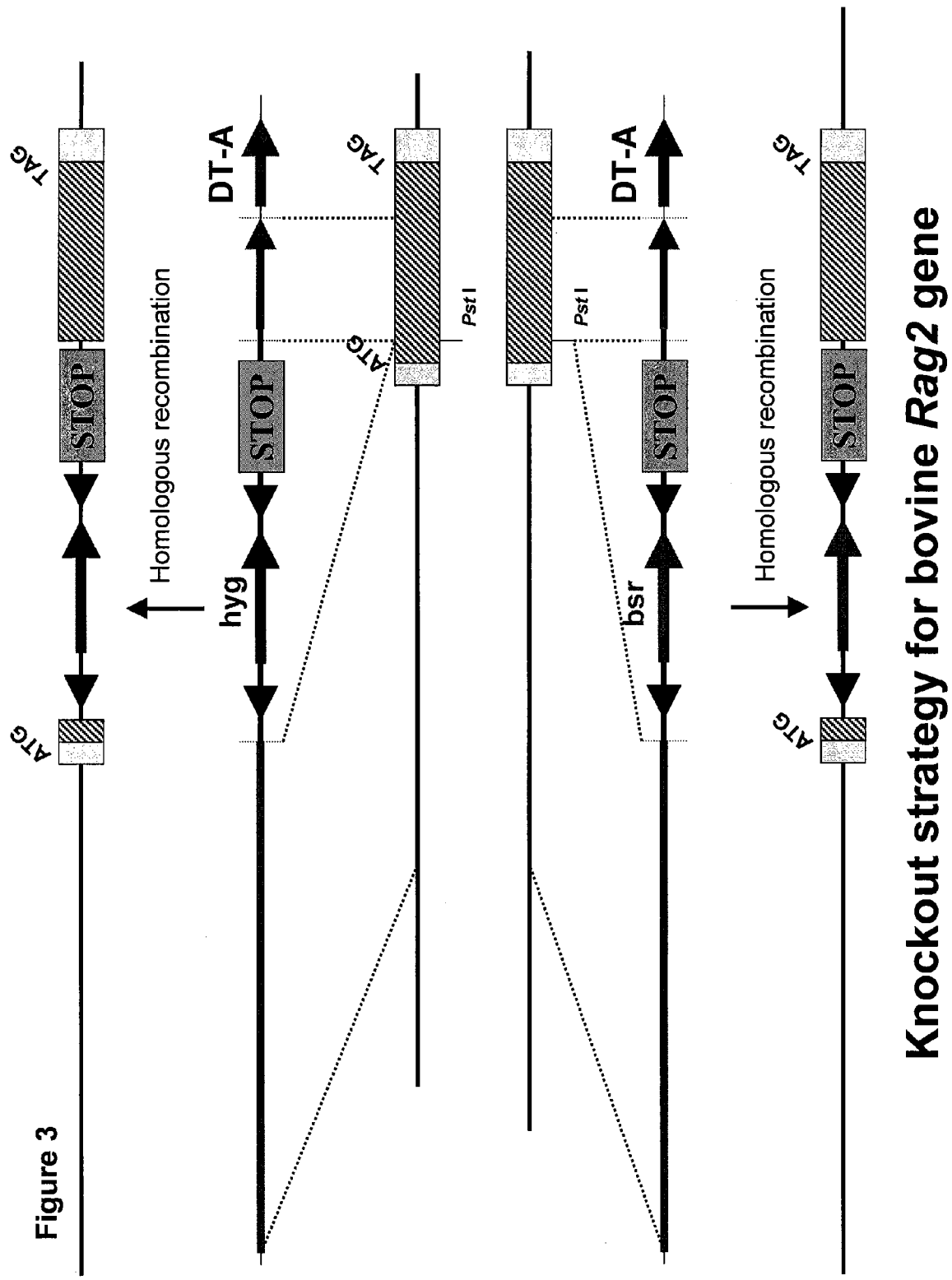
FIG. 3. This figure is a schematic diagram showing the knockout strategy for inactivating both alleles of the bovine rag-2 gene by homologous recombination using the pR2KObsr and pR3KOhyg targeting vectors.

The present invention relates to the production of xenogeneic antibodies, preferably human, canine, feline, or murine antibodies in large agricultural animals, i.e., ungulates, and other large hoofed animals such as bovines, pigs, horses, sheep, buffalo, and goats. As noted previously, the immune system poses a major barrier to the introduction of xenogeneic hematopoietic stem cells such as those of human origin into non-human animals. The present inventors remove this barrier in cattle by targeted disruption of both copies of at least one gene which is essential for functional B-cells, preferably IgM heavy chain, Igα, EBF (a transcription factor essential for B-cell development (O'Riordan et al., *Immunity* 11:21-31 (1999)); E2A (another transcription factor essential for B-cell development) (Bain et al., *Cell* 79:885-892 (1994)), and BSAP (still another transcription factor essential for B-cell development (Urbanek et al., *Cell* 79:901-912 (1994)). For example, in the case of rag knockout animals, they are unable to conduct the gene rearrangements that are necessary to generate the antigen receptors of B- or T-lymphocytes. Consequently, they do not develop endogenous B- or T-lymphocytes. Because they will not produce endogenous B- and T-lymphocytes, these rag-1 or rag-2 knockout cattle should not reject human or other species hematopoietic stem cells, and human B-cells that develop from them should proceed by mechanisms that employ antibody or cytotoxic T-cells. The development of human T-cells and human immunoglobulins should also proceed in these animals.

More specifically, the present invention provides a method for producing xenogeneic, preferably human antibodies, in a cloned animal, such as an ungulate, which comprises producing a cloned non-human animal which has been genetically modified to delete or inactivate both copies of at least one gene essential for B-cell production, e.g., Igα, IgM (mu), BSAP, E2A, EBF, rag-1, or rag-2 gene. These cloned non-human animals are engrafted in utero or shortly after birth with xenogeneic hematopoietic stem cells, e.g., human, canine, feline, or murine stem cells such as mouse, or rat. Most preferably, human hematopoietic stem cell-enriched preparations obtained from human umbilical cord or peripheral blood are used for engraftment. After such administration, these cloned animals ideally will comprise xenogeneic human B- and T-lymphocytes stably engrafted and will not produce endogenous B-cells.

When responding to immunogenic antigens naturally encountered by the non-human host or when specifically immunized, these engineered animals will make xenogeneic, preferably human antibodies in xenogeneic, preferably human B lineage cells. Large amounts of antibody will be produced because there will be complete compatibility between human antibody genes and the intracellular factors that regulate their expression. The antibodies produced should have the post-translational modifications (glycosylation patterns, etc.) that are typical of human antibodies made in human systems. Immune responses should be efficient because the T-cell help will be provided by compatible T-cells, e.g., human T-cells. Furthermore, a variety of useful classes of xenogeneic, preferably human antibodies of high affinity can be produced because the intracellular factors that regulate switching and somatic mutation-driven affinity maturation are compatible with the xenogeneic, preferably human antibody genes. The presence of compatible T-cells should enable and facilitate antibody class switching and the somatic hypermutation of rearranged antibody genes.

Therefor, in one embodiment, the present invention involves producing a cloned genetically engineered or transgenic ungulate, in which the expression of both copies of a desired gene essential for B-cell production, e.g., Igα, EBF, E2A, or BSAP, the IgM, rag-1, or rag-2 gene has been knocked out. This is effected by genetically modifying a cell obtained from such animal in vitro, using an appropriate targeting construct, and using the resulting genetically modified cell or nucleus, as a nuclear donor for nuclear transfer by fusing or inserting such cell or nucleus into a suitable recipient cell, e.g., a cell in metaphase II, preferably an oocyte or blastomere. Suitable genetically modified cells include germ cells, embryonic cells, and differentiated (somatic) cells, and most preferably will comprise differentiated cells. Differentiated ungulate cells according to the present invention are those cells which are past the early embryonic disc stage (in the case of bovines corresponds to day 10 of bovine embryogenesis). Suitable differentiated cells may be derived from ectoderm, mesoderm, or endoderm.

Suitable donor cells may be obtained by known methods. Examples of differentiated donor cells useful in the present invention include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the donor cells used for nuclear transfer may be obtained from different organs, e.g., skin, lung, pancreas, liver, stomach, intestine, heart, reproductive organs, bladder, kidney, urethra, and other urinary organs, etc. These are just examples of suitable donor cells. Suitable donor cells, i.e., cells useful in the subject invention, may be obtained from any cell or organ of the body. This includes all somatic or germ cells, and also includes embryonic stem and germ cells, e.g., primordial germ cells.

Standard protocols for constructing knockout animals are provided, for example, in Thomas, K. R. et al., "High frequency targeting of genes to specific sites in the mammalian genome," Cell 44:419-428 (1986); Thomas, K. R. et al., "Site-directed mutagenesis by targeting in mouse embryo-derived stem cells," Cell 51:503-512 (1987); and Mansour, S. L. et al., "Disruption of the proto-oncogene int-2 in mouse embryo-derived stem cells: a general strategy for targeting mutations to non-selectable genes," Nature 336:348-352 (1988). As noted previously, obtaining a double knockout in primary cell lines with limited life spans in culture is difficult and uncertain. The present inventors have solved this problem in ungulates by modifying these standard protocols.

Preferably, fibroblast cells, most preferably fetal fibroblasts, will be genetically modified to obtain an ungulate cell which is homozygous for a gene essential for B-cell production, e.g., Igα, E2A, EBF, BSAP, IgM, rag-1, or rag-2 deletion. Fibroblast cells are an ideal cell type because they can be obtained from developing fetuses and adult animals in large quantities. Fibroblast cells have recently been reported to be well suited for use in cloning procedures. Of importance herein, these cells can be easily propagated in vitro with a rapid doubling time and can be clonally propagated permitting their use in gene targeting procedures.

In the present invention fibroblast cells or other suitable non-cells obtained from a particular ungulate, e.g., a bovine, are contacted, e.g., by transfection with a first vector construct that is designed such that it homologously recombines with one copy of a gene essential for B-cell production, and resulting in the inactivation thereof. Typically, the targeting construct will comprise portions of the targeted gene, an intervening sequence that is inserted in place of the target gene, and at least one marker gene that provides for selection of homologous recombinants. The DNA construct is introduced into the cell by known means, e.g., transfection, microinjection, electroporation, and transformation. Thus, in the invention the DNA of a desired ungulate cell, e.g., a bovine fibroblast, is contacted with a DNA construct that homologously recombines a gene involved in B-cell production with the bovine genome and results in the targeted deletion or inactivation of one copy of the target gene, e.g., IgM, Igα, rag-1, rag-2, EBF, E2A or BSAP. An exemplary targeting constructs for effecting deletion of the rag-2 gene are depicted in FIGS. 1 and 3. Methods for constructing vectors and the use thereof for effecting targeted deletion by homologous recombination are the subject of numerous patents which are incorporated by reference herein. These patents include e.g., U.S. Pat. Nos. 6,143,566; 06,139,835; 6,074,853; 6,010,908; 5,998,144; 5,981,214; 5,945,334; 5,925,544; 5,783,385; 5,731,411; 5,721,367; 5,776,744; 5,614,396; 5,574,2_5; 5,527,674; 5,204,244; and 5,468,629.

Successfully genetically modified cells, preferably fibroblasts, or DNA therefrom which are hemizygous for the target gene, e.g., Igα, E2A, EBF, BSAP, IgM, rag-1, or rag-2 gene, are then inserted or fused with suitable recipient cells, preferably enucleated oocytes or blastomere, using standard nuclear transfer techniques. The resulting nuclear transfer units are then allowed to develop, preferably until about the 40 day gestation state or later, at which point donor cells are obtained therefrom, e.g., fetal fibroblast cells and these cells are subject to a second round of gene targeting. The second vector construct, typically comprises the same DNA sequences as the first vector construct except that it comprises a different selective marker than used in the first construct. This vector is introduced into donor cells, e.g., fetal fibroblast cells again by known methods, e.g., transfection. Double knockout cells, e.g., fibroblast cells or cell nucleus are obtained are then fused or inserted into suitable recipient cells, preferably enucleated oocytes, again using standard nuclear transfer techniques known in the art. The resulting embryos are allowed to develop fully, in utero. Isolation of double knockout cells can be confirmed, e.g., by known detection methods, e.g., PCR.

Alternatively, male and female cell lines are obtained wherein one copy of a gene essential for B-cell production is knocked out or inactivated, e.g., EBF, E2A, BSAP, Igα, IgM, rag-1, or rag-2 as described, these male and female cell lines or DNA therefrom are each used as donor cells or nuclei for nuclear transfer to respectively produce a cloned female and male animal that comprises one copy of the IgM, rag-1, or rag-2 gene knocked out, or inactivated, the cloned animals are mated, and progeny are selected wherein both copies of the targeted gene, e.g., E2A, Igα, EBF, BSAP, IgM, rag-1, or rag-2 gene have been knocked out or inactivated. Again cells that are knockout can be confirmed by PCR detection methods.

In the present invention, suitable ungulate and hooved animals include by way of example sheep, cows, pigs, horses, guar, antelope, caribou, deer, goats, buffalo, etc. Methods for obtaining oocytes from such animals suitable for use in nuclear transfer are well known in the art. Preferably, large ungulates, and most preferably bovines will be cloned.

Additionally, nuclear transfer techniques or nuclear transplantation techniques are also known in the literature. See, in particular, Campbell et al., *Theriogenology* 43:181 (1995); Collas et al., *Mol. Report. Dev.* 38:264-267 (1994); Keefer et al., *Biol. Reprod.* 50:935-939 (1994); Sims et al., *Proc. Natl. Acad. Sci., USA* 90:6143-6147 (1993); WO 94/26884; WO 94/24274, and WO 90/03432, which are incorporated by reference in their entirety herein. Also, U.S. Pat. Nos. 4,944,384 and 5,057,420 describe procedures for bovine nuclear transplantation.

A particularly preferred method is disclosed in recently issued U.S. Pat. No. 5,945,577, the contents of which are incorporated by reference herein. This patent contains claims directed to the use of proliferating somatic cells or nuclei as donors for nuclear transfer. Alternatively, quiescent donor cells or nuclei therefrom can be used as donors for nuclear transfer as discussed by Ian Wilmut and Keith Campbell in WO 09707668A, WO 09707669A1, WO 00018902A1 and WO 00022098A1, all of which are incorporated by reference in their entirety herein.

As noted, methods for isolation of oocytes suitable for use as recipient cells in nuclear transfer are also well known in the art. Typically, this will comprise isolating oocytes from the ovaries or reproductive tract of an ungulate or other hooved mammal, e.g., a bovine. A readily available source of bovine oocytes is slaughterhouse materials.

For the successful use of techniques such as genetic engineering, nuclear transfer and cloning, oocytes are generally matured in vitro before these cells are used as recipient cells for nuclear transfer. This process generally requires collecting immature (prophase I) oocytes from suitable, e.g., ungulate ovaries, specifically bovine ovaries obtained at a slaughterhouse, and maturing the oocytes in a maturation medium prior to fertilization or enucleation until the oocyte attains the metaphase II stage, which in the case of bovine oocytes generally occurs about 18-24 hours post-aspiration. For purposes of the present invention, this period of time is known as the "maturation period." As used herein for calculation of time periods, "aspiration" refers to aspiration of the immature oocyte from ovarian follicles.

Alternatively, metaphase II stage oocytes, which are matured in vivo can be used for nuclear transfer. For example, mature metaphase II oocytes are collected surgically from either non-superovulated or superovulated cows or heifers 35 to 48 hours past the onset of estrus or past the injection of human chorionic gonadotropin (hCG) or similar hormone.

The stage of maturation of the oocyte at enucleation and nuclear transfer can affect the success of NT methods. (See, e.g., Prather et al., *Differentiation*, 48:1-8, (1991)). In general, successful mammalian embryo cloning practices use the metaphase II stage oocytes as the recipient cell because at this stage it is believed that the oocyte can be or is sufficiently "activated" to treat the introduced nucleus as it does a fertilizing sperm. In domestic animals, and especially cattle, the oocyte activation period generally ranges from about 16-52 hours, preferably about 28-42 hours post-aspiration. However this may vary somewhat across different species. One skilled in the art can determine an appropriate stage of maturation For example, immature oocytes may be washed in buffered hamster embryo culture medium (HECM) as described in Seshagine et al., *Biol. Reprod.* 40:544-606, (1989), and then placed into drops of maturation medium consisting of 50 microliters of tissue culture medium (TCM) 199 containing 10% fetal calf serum which contains appropriate gonadotropins such as luteinizing hormone (LH) and follicle stimulating hormone (FSH), and estradiol under a layer of lightweight paraffin or silicon at 39° C.

After a fixed time maturation period, which ranges from about 10 to 40 hours, and preferably about 16-18 hours, the oocytes are in the case of bovine oocytes typically enucleated. Prior to enucleation the oocytes are preferably removed and placed in HECM containing 1 milligram per milliliter of hyaluronidase prior to removal of cumulus cells. This may be effected by repeated pipetting through very fine bore pipettes or by vortexing briefly. The stripped oocytes are then screened for polar bodies, and the selected metaphase II oocytes, as determined by the presence of polar bodies, are then used for nuclear transfer. Enucleation follows.

Enucleation may be effected by known methods, such as described in U.S. Pat. No. 4,994,384, which is incorporated by reference herein. For example, metaphase II oocytes are either placed in HECM, optionally containing 7.5 micrograms per milliliter cytochalasin B, for immediate enucleation, or may be placed in a suitable medium, for example an embryo culture medium such as CR1aa, plus 10% estrus cow serum, and then enucleated later, preferably not more than 24 hours later, and more preferably 16-18 hours later.

Enucleation may be accomplished microsurgically using a micropipette to remove the polar body and the adjacent cytoplasm. The oocytes may then be screened to identify those of which have been successfully enucleated. This screening may be effected by staining the oocytes with 1 microgram per milliliter 33342 Hoechst dye in HECM, and then viewing the oocytes under ultraviolet irradiation for less than 10 seconds. The oocytes that have been successfully enucleated can then be placed in a suitable culture medium.

A single ungulate cell or that of another hooved animal, preferably one that produces a large amount of blood, of the same or different species as the enucleated oocyte or a nucleus thereof will then be transferred into the perivitelline space of the enucleated oocyte used to produce the NT unit. The donor cell and the recipient cell, i.e., enucleated oocyte will be used to produce NT units according to methods known in the art. For example, the cells may be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels will open between the two cells. Due to the thermodynamic instability of such a small opening, it enlarges until the two cells become one. Reference is made to U.S. Pat. No. 4,997,384 by Prather et al. (incorporated by reference in its entirety herein), for a further discussion of this process. A variety of electrofusion media can be used including e.g., sucrose, mannitol, sorbitol, and phosphate buffered solution. Fusion can also be accomplished using Sendai virus as a fusogenic agent (Graham, *Wister Inot. Symp. Monogr.* 9:19 (1969)).

In some cases (e.g., with small donor nuclei) it may be preferable to inject the nucleus directly into the oocyte rather than using electroporation fusion. Such techniques are disclosed in Collas and Barnes, *Mol. Reprod. Dev.* 38: 264-267 (1994), incorporated by reference in its entirety herein.

The NT unit may be activated by known methods. Such methods include, e.g., culturing the NT unit at sub-physiological temperature, in essence by applying a cold, or actually cool temperature shock to the NT unit. This may be most conveniently done by culturing the NT unit at room temperature, which is cold relative to the physiological temperature conditions to which embryos are normally exposed.

Alternatively, activation may be achieved by application of known activation agents. For example, penetration of oocytes by sperm during fertilization has been shown to activate prefusion oocytes to yield greater numbers of viable pregnancies and multiple genetically identical calves after nuclear transfer. Also, treatments such as electrical and chemical shock may be used to activate NT embryos after fusion. Suitable oocyte activation methods are the subject of U.S. Pat. No. 5,496,720, to Susko-Parrish et al., herein incorporated by reference in its entirety.

Additionally, activation may be effected by simultaneously or sequentially increasing levels of divalent cations in the oocyte, and reducing phosphorylation of cellular proteins in the oocyte.

This will generally be effected by introducing divalent cations into the oocyte cytoplasm, e.g., magnesium, strontium, barium, or calcium, e.g., in the form of an ionophore. Other methods of increasing divalent cation levels include the use of electric shock, treatment with ethanol and treatment with caged chelators.

Phosphorylation may be reduced by known methods, e.g., by the addition of kinase inhibitors, e.g., serine-threonine kinase inhibitors, such as 6-dimethylaminopurine, staurosporine, 2-aminopurine, and sphingosine.

Alternatively, phosphorylation of cellular proteins may be inhibited by introduction of a phosphatase into the oocyte, e.g., phosphatase 2A and phosphatase 2B.

A preferred protocol procedure involves the use of cycloheximide and cytochalasin D and the media described below. It shall be noted that this is exemplary of suitable activation methods and media, and is not essential to the invention:

Preparation of Activation, and Culture Plate

An activation plate is commenced by combining 500 µl of ACM media (described below), 2.5 µl CHX, 0.5 µl Cytochalasin D, on a tissue culture plate, and by placement of activation media in 35 µl micro drops which are treated with mineral oil, just until the tops of the drops become covered.

Thereafter, a 1% FCS culture plate for day 0 to day 4 old embryos is prepared by combining 500 µl ACM plus 5 µl FCS. This is again effective using tissue plates prepared using 35 ml which are cover micro drops of 35 µl with oil. The activation and culture plates are then equilibrated for a minimum of 2 hours before transferring the oocytes or embryos to another plate.

Preparing Oocytes for Activation

After oocytes have matured (at least 20 hours) they are stripped of their cumulus cells to facilitate activation. This is affected by use of a solution of hyaluronidase and TLHepes in an amount appropriate to effect activation. Two ml of the activate solution are aliquoted into a 35-mm petri dish to rinse oocytes after removal from maturation media. Another 2 ml is used for stripping and is placed in a 15 ml conical tube. Typically, up to 200-300 oocytes may be stripped in two volume of media.

Oocytes are then removed from maturation media while collecting as little fluid as possible and are transformed to a hyaluronidase rinse plate. Oocytes allowed to soak for approximately 2-3 minutes, with the swirling plate often in order to dilute the maturation media and rinse oocytes. Oocytes are removed from rinse plate and placed in 15 ml conical for vortexing. Vortexing is used to strip oocytes, e.g., for about 5-6 minutes at a medium speed (Fisher Vortex-Genie 2).

After vortexing oocytes are placed on a 35 mm petri plate and rinsed in a 15 ml tube using 2 ml TLHepes also placed in the same dish. Oocytes are retrieved and rinsed using 2 ml TLHepes. If the oocytes are younger than 24 hours when stripped, they preferably are placed into equilibrated ACM and held in an incubator until at lest about 24 hours old.

Ionomycin Treatments and Subsequent Rinses

Oocytes preferably are approximately 24-30 hours old upon activation. Activation is preferably effected by use of a 2 ml solution of Z-1 media and ionomycin which is allowed to warm on a heating stage, under an opaque cover to eliminate light, for about 2-3 min. The media is then heated to approximately 38° C., and oocytes to be activated are transferred into ionomycin solution for about 4 minutes. After about 4 minutes has elapsed oocytes are removed from media and immediately place in TLHepes to rinse. After about 3-4 rinses, oocytes are transferred to an equilibrated activation plate and incubated for about 6 hours.

Activation Plate Incubation and Rinses to Culture Plates

After incubation period is completed, oocytes are removed from activation plates and again rinsed, preferably about 4 times in TLHepes. After the rinses are completed, the oocytes are transferred into ACM+1% FCS culture plates, and then incubated until day 4 (activation date=d0).

On day 4, four culture plates are prepared by combining 500 μl ACM and 50 μl FCS. After thorough mixing the media is placed as micro drops (35 μl) onto a tissue culture plate, which again is covered in mineral oil and incubated preferably for a minimum of about 2 hours to equilibrate. The oocytes are transferred directly from the first culture plate on the second (ACM+10% FCS), and oocytes/embryos are then counted. The cleavage rate is calculated by taking the number of embryos cleaved and dividing by the number of oocytes initially activated. At days 7, and 8, embryos are observed for blastocyst formation and additional embryo that contain blastocoel are counted. The blastocyst rate is obtained by dividing the number of blastocysts by the number of oocytes originally activated, to obtain the blastocyst rate.

Media and formulations used in above described activation procedures:

| ACM Media | |
|---|---|
| NaCl | 0.580 g |
| NaHCO$_3$ | 0.209 g |
| KCl | 0.022 g |
| L-glutamine | 0.015 g |
| *CaCl$_2$ 2H$_2$0 | 0.004 g |
| Pyruvic Acid | 2 ml |
| BME | 2 ml |
| MEM | 1 ml |
| Pen/Strep | 1 ml |
| Lactic Acid | 14 μl |
| Phenol Red | 100 μl |
| BSA (fatty acid free) | 0.300 g |

| Z-1 Media | |
|---|---|
| H$_2$0 | 500 ml |
| NaCl | 3.300 g |
| KCl | 0.120 g |
| NaHCO$_3$ | 0.084 g |
| NaH$_2$Po$_4$H$_2$O | 0.024 g |
| *CaCl$_2$ 2H$_2$0 | 0.150 g |
| *MgCl$_2$ 6H$_2$0 | 0.050 g |
| Hepes | 1.200 g |
| Pen/Strep | 5 ml |
| Lactic Acid | 930 μl |
| Phenol Red | 500 μl |
| BSA (fatty acid free) | 0.500 g |

| TLHepes | |
|---|---|
| H20 | 500 ml |
| NaCl | 3.300 g |
| KCl | 0.120 g |
| NaHCO$_3$ | 0.084 g |
| NaH$_2$Po$_4$H$_2$O | 0.024 g |
| *CaCl$_2$ 2H$_2$0 | 0.150 g |
| *MgCl$_2$ 6H$_2$0 | 0.050 g |
| Hepes | 1.200 g |
| Pen/Strep | 5 ml |
| Lactic Acid | 930 μl |
| Phenol Red | 500 μl |
| BSA (fatty acid free) | 0.500 g |

| Ionomycin Activation Media | |
|---|---|
| Z-1 Media | 2 ml |
| Ionomycin | 2 μl |

Hyaluronidase Solution for Stripping Oocytes
1 ml TLHepes/1 mg Hyaluronidase

| Activation Media Plates | |
|---|---|
| ACM | 500 μl |
| Cycloheximide | 2.5 μl |
| Cytochalasin D | 0.5 μl |

| Culture Plate d0-d4 | |
|---|---|
| ACM | 500 μl |
| FCS | 5 μl |

| Culture Plate d4 d8 | |
|---|---|
| ACM | 500 μl |
| FCS | 5 μl |

Activated NT units can be cultured in a suitable in vitro culture medium until the generation of CICM cells and cell colonies. Culture media suitable for culturing and maturation of embryos are well known in the art. Examples of known media, which may be used for bovine embryo culture and maintenance, include Ham's F-10+10% fetal calf serum (FCS), Tissue Culture Medium-199 (TCM-199)+10% fetal calf serum, Tyrodes-Albuminate-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb serum, or steer serum. A preferred maintenance medium includes TCM-199 with Earl salts, 10% fetal calf serum, 0.2 mM Na pyruvate, and 50 μg/ml gentamicin sulphate. Any of the above may also involve co-culture with a variety of cell types such as granulosa cells, oviduct cells, BRL cells, uterine cells, and STO cells.

Another maintenance medium is described in U.S. Pat. No. 5,096,822 to Rosenkrans, Jr. et al., which is incorporated herein by reference. This embryo medium, named CR1, contains the nutritional substances necessary to support an embryo.

Afterward, the cultured NT unit or units are preferably washed and then placed in a suitable media containing FCS well plates which preferably contain a suitable confluent feeder layer. Suitable feeder layers include, by way of example, fibroblasts and epithelial cells, e.g., fibroblasts and uterine epithelial cells derived from ungulates, chicken fibroblasts, murine (e.g., mouse or rat) fibroblasts, STO and SI-m220 feeder cell lines, and BRL cells.

The NT units are cultured on the feeder layer until the NT units reach a size suitable for transferring to a recipient female, or for obtaining cells which may be used to produce CICM cells or cell colonies. Preferably, these NT units will be cultured until at least about 2 to 400 cells, more preferably about 4 to 128 cells, and most preferably at least about 50 cells. Culturing is preferably effected under suitable conditions, i.e., about 38.5° C. and 5% $CO_2$, with the culture medium changed in order to optimize growth typically about every 2-5 days, preferably about every 3 days.

The methods for embryo transfer and recipient animal management utilized in the present invention are standard techniques for the embryo transfer industry. Synchronous transfers are advantageous to the success rate, i.e., in development of viable offspring after embryo transfer, i.e., the stage of the NT embryo is in synchrony with the estrus cycle of the recipient female. This advantage and how to maintain recipients are reviewed in Siedel, G. E., Jr. ("Critical review of embryo transfer procedures with cattle" in *Fertilization and Embryonic Development* in Vitro (1981), L. Mastroianni, Jr. and J. D. Biggers, Ed., Plenum Press, New York, N.Y., page 323), the contents of which are hereby incorporated by reference. Preferably, activation and culturing is effected using cycloheximide and cytochalasin Dc8 described in the example.

According to the invention, ungulates which do not express endogenous antibodies, because of inactivation or knockout of a gene essential for B-cell production, e.g., Igμ, Igm (mu), E2A, EBF, BSAP, rag-1, or rag-2, will be injected in utero or shortly after birth, typically within about one week, and more preferably within the first 48 hours after birth, with xenogeneic hematopoietic stem cells. Methods for purifying such xenogeneic, preferably murine, canine, feline, or human, or non-human primate hematopoietic stem cells are well known. Such methods typically use ligands that bind to stem cell markers. Such markers include CD34 and Thy-1. Known purification methods include flow cytometry, negative selection, immuno-purification, etc. For example, WO 99/23205 recently filed by Dick et al., discloses a method for producing purified human hematopoietic stem cells from peripheral blood and cord blood. Other methods are described in U.S. Pat. Nos. 5,763,197; 5,981,708; 5,763,266; and 5,914,108, incorporated by reference herein.

These animals are injected preferably with about $10^7$-$10^8$ cells of a preparation of enriched hematopoietic stem cells, preferably human. It is anticipated that this will be sufficient to "reconstitute" the immune system of an ungulate, e.g., a cow, with xenogeneic (human) B- and T-cells. This may be affected via a single or multiple administration, e.g., if stable engraftment does not result after initial injection of stem cells. Also, higher cell numbers may be administered if necessary. Additionally, to facilitate engraftment of donor cells, cytokines or stromal cells may additionally be administered as this may facilitate the development of human or other stem cells into lymphoid lineages. This may be effected by administration of appropriate (homologous) hematopoietic cytokines, e.g., any of the interleukins, e.g., IL-1, IL-2, IL-3, IL-4, IL-5, IL-6, IL-7, IL-8, IL-9, IL-10, IL-11, IL-12, colony stimulating factors, such as GM-CSF, and others, e.g., erythropoietin. Alternatively, a gene encoding appropriate cytokines may be introduced during genetic modification of target cells. Alternatively or additionally, homologous bone marrow stromal cells may be introduced. These cytokines and stromal cells may be administered repeatedly before, simultaneously, or after stem cell infusion.

After the hematopoietic stem cells have been stably engrafted, the ungulates, e.g., bovine, can be used to produce antibodies against desired antigens. These antigens include those to which the animal is naturally exposed, or antigens that are administered by exogenous means, e.g., by injection. Suitable antigens broadly include any antigen to which an antibody, e.g., human antibody, is desirably produced against. These antigens include by way of example antigens specific to infectious agents, such as viruses, bacteria, fungi, yeast, allergens, antigens expressed by tumor cells, disease markers, cytokines, signaling molecules, therapeutic agents, enzymes, cytokines, growth factors, and lectins, among others.

After the stably engrafted animal, e.g., an IgM, rag-1, Igα, E2A, BSAP, EBF, rag-2 knockout ungulate has been exposed to factors, the antigen, the animal should elicit an immune response against such antigen resulting in the production of xenogeneic, e.g., human antibodies against such antigen. The serum from the animal, e.g., a bovine, which contains such antibodies can be used for effecting passive immunization against the antigen. Alternatively, the antibodies can be purified and isolated from the animal's serum by well known methods. These antibodies can be either monoclonal or polyclonal antibodies. Alternatively, the B-cells can be isolated from the bovine and immortalized by fusing with, for example, myeloma cells, and the monoclonal antibodies secreted by these cells can be isolated using well known methods.

The following examples are presented in order to more fully illustrate the preferred embodiments of the invention. They should in no way be construed, however, as limiting the broad scope of the invention.

Example 1

Generation of Igm Knockout Bovine Embryos

The following procedures were used to generate bovine fibroblast cell lines in which one allele of the immunoglobulin heavy chain (mu) locus is disrupted by homologous recombination. A DNA construct for effecting IgM knockout was generated by the removal of introns 1-4 of the Mu locus which were replaced with a copy of neomycin resistance gene. Using this construct, neomycin resistant cell lines have been obtained which were successfully used in nuclear transfer procedures and blastocysts from these cell lines have been implanted into recipient cows. Additionally, some of these blastocysts were tested to confirm that targeted insertion into has occurred appropriately in the mu locus using PCR procedures. Blastocysts resulting from nuclear transfer procedures from several of the cell lines obtained indicated that heterozygous IgM-KO fetuses are in gestation. Additionally, both male and female cell lines that comprise a single IgM (mu) knockout have been produced. It is anticipated that mating of animals cloned from these cell lines will give rise to progeny wherein both copies of mu are inactivated. These procedures are discussed in greater detail below.

DNA Construct

Figure 5:
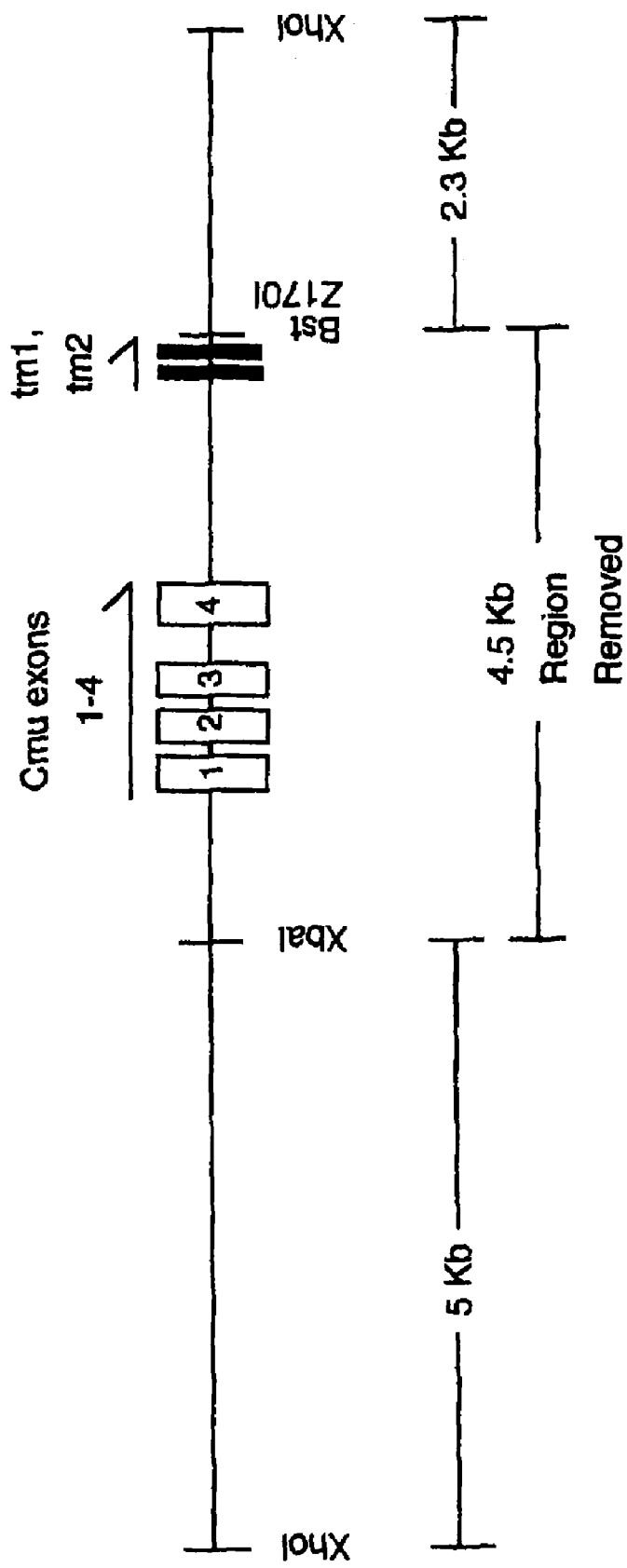
FIG. 5. This figure depicts the targeting strategy for inactivating both alleles of the bovine Igμ gene.

The DNA used in all transfections described in this document was generated as follows:

The four main exons (excluding the transmembrane domain exons), CH1-4, are flanked by an XhoI restriction site at the downstream (CH4) end and an XbaI site at the upstream (CH1) end. The construct used for the transfection procedure consists of 1.8 kb of genomic sequence downstream of the XhoI site and 3.1 kb of genomic sequence upstream of the XbaI site. A neomycin resistance marker was inserted between these two fragments on a 3.0 kb fragment, replacing 2.4 kb of DNA, originally containing CH1-4, from the originating genomic sequence. The backbone of the vector is pBluescriptII SK+ (Stratagene) and the insert of 8.9 kb was purified and used for transfection of bovine fetal fibroblasts. This construct is shown in FIG. 5.

Transfection/Knockout Procedures

Transfection of fetal bovine fibroblasts was performed using a commercial reagent Superfect Transfection Reagent (Qiagen, Valencia, Calif., USA), Catalog Number 301305.

Bovine fibroblasts were generated from disease-tested cattle at Hematech of Kansas/Cyagra of Kansas, sent to Hematech's Worcester Molecular Biology Labs and used for all experiments described.

The medium used for culture of bovine fetal fibroblasts consisted of the following components:
- 500 ml Alpha MEM (Bio-Whittaker #12-169F)
- 50 ml fetal calf serum (Hy-Clone #A-1111-D)
- 2 ml antibiotic/antimyotic (Gibco/BRL #15245-012)
- 1.4 ml 2-mercaptoethanol (Gibco/BRL #21985-023)
- 5.0 ml L-Glutamine (Sigma Chemical #G-3126)
- 0.5 ml tyrosine tartrate (Sigma Chemical #T-6134)

On the day prior to transfection procedures, cells were seeded in 60-mm tissue culture dishes with a targeted confluency of 40-80% as determined by microscopic examination.

On the day of transfection, 5 μg of DNA, brought to a total volume of 150 μl in serum-free, antibiotic-free medium), was mixed with 20 μl of Superfect transfection reagent and allowed to sit at room temperature for 5-10 minutes for DNA-Superfect complex formation. While the complex formation was taking place, medium was removed from the 60-mm tissue culture dish, containing bovine fibroblasts to be transfected, and cells were rinsed once with 4 ml of phosphate-buffered saline. One milliliter of growth medium was added to the 170 μl DNA/Superfect mixture and immediately transferred to the cells in the 60-mm dish. Cells were incubated at 38.5° C., 5% $CO_2$ for 2.5 hours. After incubation of cells with the DNA/Superfect complexes, medium was aspirated off and cells were washed four times with 4 ml PBS. Five ml of complete medium were added and cultures were incubated overnight at 38.5° C., 5% $CO_2$. Cells were then washed once with PBS and incubated with one ml of 0.3% trypsin in PBS at 37° C. until cells were detached from the plate, as determined by microscopic observation. Cells from each 60-mm dish were split into 24 wells of a 24-well tissue culture plate (41.7 ul/well). One milliliter of tissue culture medium was added to each well and plates were allowed to incubate for 24 hours at 38.5° C. and 5% $CO_2$ for 24 hours.

During all transfection procedures, sham transfections were performed using a Superfect/PBS mixture containing no DNA, as none of those cells would be expected to contain the neomycin resistance gene and all cells would be expected to die after addition of G418 to the tissue culture medium. This served as a negative control for positive selection of cells that received DNA.

After the 24 hour incubation, one more milliliter of tissue culture medium containing 400 μg/ml G418 was added to each well, bringing the final G418 concentration to 200 ug/ml. Cells were placed back into the incubator for 7 days of G418 selection. During that period, both transfected and sham transfection plates were monitored for cell death and over 7 days, the vast majority of wells from the sham transfections contained few to no live cells while plates containing cells that received the DNA showed excellent cell growth.

After the 7 day selection period, the cells from wells at 90-100% confluency were detached using 0.2 ml 0.3% trypsin in PBS and were transferred to 35-mm tissue culture plates for expansion and incubated until they became at least 50% confluent, at which point, cells were trypsinized with 0.6 ml 0.3% trypsin in PBS. From each 35-mm tissue culture plate, 0.3 ml of the 0.6 ml cell suspension was transferred to a 12.5-$cm^2$ tissue culture flask for further expansion. The remaining 0.3 ml was reseeded in 35-mm dishes and incubated until they attained a minimal confluency of approximately 50%, at which point cells from those plates were processed for extraction of DNA for PCR analysis. Flasks from each line were retained in the incubator until they had undergone these analyses and were either terminated if they did not contain the desired DNA integration or kept for future nuclear transfer and cryopreservation.

Screening for Targeted Integrations

As described above the DNA source for screening of transfectants containing the DNA construct was a 35-mm tissue culture dish containing a passage of cells to be analyzed. DNA was prepared as follows and is adapted from a procedure published by Laird et al. (Laird et al., "Simplified mammalian DNA isolation procedure", *Nucleic Acids Research*, 19:4293). Briefly, DNA was prepared as follows:

A cell lysis buffer was prepared with the following components:
- 100 mM Tris-HCl buffer, pH 8.5
- 5 mM EDTA, pH 8.0
- 0.2% sodium dodecyl sulfate
- 200 mM NaCl
- 100 μg/ml Proteinase K Medium was aspirated from each 35-mm tissue culture dish and replaced with 0.6 ml of the above buffer. Dishes were placed back into the incubator for three hours, during which cell lysis and protein digestion were allowed to occur. Following this incubation, the lysate was transferred to a 1.5 ml microfuge tube and 0.6 ml of isopropanol was added to precipitate the DNA. Tubes were shaken thoroughly by inversion and allowed to sit at room temperature for 3 hours, after which the DNA precipitates were spun down in a microcentrifuge at 13,000 rpm for ten minutes. The supernatant from each tube was discarded and the pellets were rinsed with 70% ethanol once. The 70% ethanol was aspirated off and the DNA pellets were allowed to air-dry. Once dry, each pellet was resuspended in 30-50 μl of Tris (10 mM)-EDTA (1 mM) buffer, pH 7.4, and allowed to hydrate and solubilize overnight. 5-7 microliters of each DNA solution was used for each polymerase chain reaction (PCR) procedure.

Two separate PCR procedures were used to analyze transfectants. The first procedure used two primers that were expected to anneal to sites that are both located within the DNA used for transfection. The first primer sequence is homologous to the neomycin resistance cassette of the DNA construct and the second is located approximately 0.5 kb away, resulting in a short PCR product of 0.5 kb. This reaction was used to verify that cells surviving G418 selection were resistant as a result of integration of the DNA construct.

Because only a small percentage of transfectants would be expected to contain a DNA integration in the desired location (the Mu locus), another pair of primers was used to determine not only that the DNA introduced was present in the genome of the transfectants but also, that it was integrated in the desired location. The PCR procedure used to detect appropriate integration was performed using one primer located within the neomycin resistance cassette of the DNA construct and one primer that would be expected to anneal over 1.8 kb away, but only if the DNA had integrated at the appropriate site of the IgM locus (since the homologous region was outside the region included in the DNA construct used for transfection). The primer was designed to anneal to the DNA sequence immediately adjacent to those sequences represented in the DNA construct if it were to integrate in the desired location (DNA sequence of the locus, both within the region present in the DNA construct and adjacent to them in the genome was previously determined).

Using these methods, 135 independent 35-mm plates were screened for targeted integration of the DNA construct into the appropriate locus. Of those, DNA from eight plates were determined to contain an appropriately targeted DNA construct and of those, three were selected for use in nuclear transfer procedures. Those cells lines were designated as "8-1C", "5-3C" and "10-1C." Leftover blastocysts not used for transfer into recipient cows were used to extract DNA which was subjected to additional PCR analysis. This analysis was effective using a nested PCR procedure using primers that were also used for initial screening of transfected lines.

As noted above, three cell lines were generated using the gene targeting construct designed to remove exons 1-4 of the mu locus. These lines all tested positive for targeted insertions using a PCR based test and were used for nuclear transfers. Leftover blastocysts resulting from those nuclear transfers were screened by PCR testing the appropriately targeted construct. The following frequencies of positive blastocysts were obtained:

Cell Line 8-1C: 6/8
Cell Line 10-1C: 2/16
Cell Line 5-3C: 0/16

Although at forty days of gestation, 11 total pregnancies were detected by ultrasound, by day 60, 7 fetuses had died. The remaining 4 fetuses were processed to regenerate new fetal fibroblasts and remaining organs were used to produce small tissue samples for PCR analysis. The results of the analyses are below:

Line 8-1C: two fetuses, one fetus positive for targeted insertion by PCR
Line 10-1C: one fetus, positive for targeted insertion by PCR
Line 5-3C: one fetus, negative for targeted insertion by PCR Surprisingly, although the frequency of 10-1C blastocysts testing positive for targeted insertion was only 2/16, the one viable 60-day fetus obtained from that cell line was positive as determined by PCR. A positive fetus from 8-1C was also obtained. Southern blot analysis of DNA of all tissue samples is being effected to verify that the construct not only targeted correctly at one end (which is determined by PCR of the shorter region of homology present in the original construct) but also at the other end. Based on results to date, it is believed that two heavy chain knockout fetuses from two independent integration events have been produced. Also, since these fetuses were derived from two different lines, at least one is likely to have integrated construct correctly at both ends. Once the Southern blot analyses have confirmed appropriated targeting of both ends of targeting construct, further nuclear transfers will be performed to generate additional fetuses which will be carried to term.

Nuclear Transfer and Embryo Transfer

Nuclear transfers were performed with the K/O cell line (8-1-C (18)) and eight embryos were produced. A total of six embryos from this batch were transferred to three disease free recipients at Trans Ova Genetics ("TOG").

Frozen embryos have been transferred to ten disease free recipients to obtain disease free female fibroblast cell lines. Fetal recoveries will be scheduled after confirming the pregnancies at 35-40 days.

Pregnancy Diagnosis and Fetal Recovery

Pregnancy status of the eighteen recipients transferred with cloned embryos from knockout fetal cells was checked by ultrasonography.

| Clone ID | No of recips transferred | Pregnancy at 40 days (%) |
|---|---|---|
| 8-1-0C | 5 | 4 (80) |
| 10-1-C | 6 | 4 (67) |
| 5-3-C | 5 | 3 (60) |
| Total | 16 | 11 (69) |

Pregnancy Diagnosis

Pregnancy status of the three recipients transferred with cloned embryos from knockout cells (8-1C) was checked, one was open and the other two have to be reconfirmed next month.

Pregnancy status said 28 recipients transferred with cloned embryos from cells containing hchr.14fg was checked by ultrasonography.

TABLE 1

| Pregnancy diagnosis | | |
|---|---|---|
| Clone ID | No of recips transferred | Pregnancy at 40 days (%) |
| 2-1 | 08 | 03 (38) |
| 4-2 | 10 | 00 (00) |
| 4-1 | 05 | 00 (00) |
| 4-1 | 03 | 01 (33) |
| 2-1 | 02 | 01 (50) |
| Total | 28 | 05 (18) |

The pregnancy rates are much lower than anticipated. This is believed to be attributable to extremely abnormally hot weather during embryo transfer.

Fetal Recoveries and Establishment of Cell Lines

Eleven pregnancies with the K/O embryos at 40 days were obtained. Four live fetuses were removed out of these at 60 days. Cell lines were established from all four and cryopreserved for future use. Also we collected and snap frozen tissue samples from the fetuses and sent them to Hematech molecular biology laboratory for PCR/Southern blot analysis.

All four of the cell lines described above (i.e., the four cell lines established from knockout embryos removed at 60 days) are male. In order to secure female, cell line, cell lines were established not cryopreserved for future establishment of K/O cells from the fetuses (six) collected at 55 days of gestation from the pregnancies established at Trans Ova Genetics with disease-free recipients. Recently, the existence confirmed the question of a female cell line containing a mu knockout was confirmed. This female cell line will be used to produce cloned animals which will be mated with animals generated from the male cell lines, and progeny screened for those that contain the double mu knockout.

Introduction of Hematopoietic Stem Cells into Transgenic Bovine IgM Knockout

Human hematopoietic stem cells (HSCs) are obtained from peripheral blood, cord blood or bone marrow. The preferred choice is cord blood. Crude cord blood fractions can be separated by centrifugation. To remove hemolyzed blood the cells are pelleted and resuspended in a buffer or the cord blood fracture can be centrifuged over a ficoll gradient separating out the hemolyzed blood, the intact RBCs and white blood fraction. Additionally, HSCs can be obtained after separation based on the CD34 cell surface marker. While the CD34 marker is not unique to HSCs, it is found in a small population of cells that contain HSCs. Approximately 1 million cells (in a volume of about 0.2 to 2.0 ml of buffer) from the crude fractions or considerably fewer (thousands) from a CD34 enriched fraction are injected into the peritoneal cavity of a 75 to 110 day bovine fetus.

The injection procedure comprises making a flank incision into a pregnant cow. The gravid fetus is exposed through the excision. The fetal abdominal area is located by palpation and by use of an ultrasound probe. An 18-gauge needle attached to an ICC syringe is inserted into the abdominal area and solution of HSCs injected. The fetus is then placed back into the abdominal cavity of the cow and the incision sutured. It is anticipated that these animals upon birth will have a human immune system, at least with respect to T- and B-cells.

Example 2

Generation of Rag-2 Knockout Bovines

The bovine rag-2 gene along with 3' and 5' flanking sequences was cloned from a bovine lambda ZapII genomic library and used to make the construct, BOVRAG-2-KO, which is shown schematically in FIG. 1. The sequence of bovine rag-2 is shown in FIG. 2. Two versions of this construct have been made. One contains a gene encoding neomycin phosphotransferase (neo) as the selectable marker and the other has puromycin-N-acetyl transferase (puro) as the selectable marker.

Additional examples of rag-2 knockout vectors that may be used to generate rag-2 knockout bovines are depicted in FIG. 3. These two KO vectors, pR2KObsr and pR3KOhyg, were constructed as follows. To isolate genomic DNA around exon 2 of the bovine rag-2 gene, a DNA probe was amplified by PCR using the following primer pair 5'-GGAGGAAAAA-CACCAAACAATGA-3' (SEQ ID NO: 1) and 5'-CTGAT-AGCCACCAACAATAACAAAT-3' (SEQ ID NO: 2) (bRag2-F and bRag2-R, respectively). Using this probe, a bovine (Holstein×Jersey) genomic λ phage library was screened, and positive λ phage clones were identified. These clones should contain both alleles of the bovine rag-2 gene. To distinguish the alleles, the obtained phage clones were subjected to sequencing and, based on polymorphic sequence, we designated the two alleles "R2" and "R3". To construct allele-specific KO vectors, R2-specific- or R3-specific-targeting vectors, we chose the #2 clone for R2 and the #3 clone for R3. For the generation of the R3-specific KO vector, 9.9 kilobases of SwaI-NotI genomic fragment around exon 2 of bovine rag-2, R3 allele was subcloned into pBluescript II SK(−) in which the KpnI and EcoRV sites had been replaced with SrfI and SwaI sites, respectively, in a two-step process (7 kb of SwaI-NotI fragment, followed by 2.2 kb of SwaI-SwaI fragment); named pR3LS. The KpnI fragment (2.4 kb) in the above genomic insert was subcloned onto pBluescript II SK (−) in which the PstI site was already disrupted. The PstI site in the 2.4 kb-fragment was replaced with a PmeI site, and then the 2.4 kb-KpnI-KpnI fragment with the PmeI site was returned to the KpnI-digested pR3LS. Next, both the hyg and STOP cassettes were inserted at the PmeI site, which is just downstream of the initial ATG of bovine rag-2 gene. Finally, a diphtheria toxin gene (DT-A, Gibco) was added to the NotI site in pR3LS. DT-A was inserted in sense orientation relative to the bsr gene in the targeting cassette to kill cells in which the targeting cassette was randomly integrated in the genome (pR3KOhyg vector). By steps similar to those described above, another KO vector for the R2 allele of bovine rag-2, containing the bsr gene, was constructed (pR2KObsr vector).

Constructs can be introduced into bovine fetal fibroblasts by electroporation using standard techniques (Morrison, S. L., *Current Protocols in Immunology*, Supplement 12:10.17.10 (1998)). Following electroporation, the cells are washed in complete medium (Alpha MEM supplemented with 10% fetal calf serum penicillin 100 IU/ml, streptomycin 100 IU/ml), resuspended to a concentration of $1 \times 10^5$ cells/ml, and distributed in 0.1 ml aliquots to the wells of 96-well culture plates. After 24 hours of incubation, an additional 0.1 ml of 2X selective medium (complete medium with G418, puromycin, hygromycin B, or blasticidin S, depending on the targeting vector) is used. The resistant clones that emerge can be screened by PCR to determine which clones contain construct-mediated disruptions of the rag-2 gene.

Transfection of bovine fibroblasts with the above vectors (pR3KOhyg and pR2KObsr) was performed using the following standard electroporation protocol. The medium used to culture the bovine fetal fibroblasts contained 500 ml Alpha MEM (Gibco, 12561-049), 50 ml fetal calf serum (Hy-Clone #ABL13080), 5 ml penicillin-streptomycin (SIGMA), and 1 ml 2-mercaptoethanol (Gibco/BRL #21985-023). On the day prior to transfection, cells were seeded on a T175 tissue culture flask with a confluency of 80-100%, as determined by microscopic examination. On the day of transfection, about $10^7$ bovine fibroblasts cells were trypsinized and washed once with alpha-MEM medium. After resuspension of the cells in 800 µl of alpha-MEM, 30 µg of the Srf I-digested KO vector (pR2KObsr vector) dissolved in Hepes buffer saline (HBS) containing 1 mM spermidine was added to the cell suspension and mixed well by pipetting. The cell-DNA suspension was transferred into an electroporation cuvette and electroporated at 550 V and 50 µF. After that, the electroporated cells were plated onto thirty 48-well plates with the alpha-MEM medium supplemented with the serum. After a 48 hour-culture, the medium was replaced with medium containing 10 µg/ml of blasticidine, and the cells were cultured for 2-3 weeks to select blasticidine resistant cells. After selection, all colonies which reached close to 100% confluency were divided into two replica plates (24-well and 48-well plates): one plate for genomic DNA extraction, and the other plate for nuclear transfer. Genomic DNA was extracted from the colonies to screen for the desired homologous recombination events by PCR.

To screen for targeted integrations, the genomic DNA was independently extracted from each well using the PURE-GENE DNA isolation Kit (Gentra SYSTEMS) according to the manufacture's protocol. Each genomic DNA sample was resuspended in 20 µl of 10 mM Tris-C1 (pH 8.0) and 1 mM EDTA. Screening by PCR was performed using the following primer pair RKObsrF (5'-GTTGATTTCAGACTATGCAC-CAGATTGTTTTG-3'; SEQ ID NO: 3) and RKObsrR (5'-AATTCCTTTGGGTGTTAGCTTCTTTACTGGTT-3'; SEQ ID NO: 4). The sequence of one primer is located in the KO vector, and the sequence of the other primer is located just outside of the integrated vector in the targeted endogenous locus. Therefore, the expected PCR product is detected only when the KO vector is integrated into the targeted locus by homologous recombination. The PCR reaction mixtures contained 17.9 µl water, 3 µl of 10X LA PCR buffer II ($Mg^{2+}$ plus), 4.8 µl of dNTP mixture, 10 pmol of forward primer, 10 pmol of reverse primer, 2 µl of genomic DNA, and 0.3 µl of LA Taq. Forty cycles of PCR were performed by incubating the reaction mixtures under the following conditions: 85° C. for three minutes, 94° C. for one minute, 98° C. for 10 seconds, and 68° C. for 6 minutes. After PCR, the reaction mixtures were analyzed by electrophoresis. Out of 100-200 screened clones, about half of them generated the expected PCR products. As a result of sequencing of the PCR products, the KO vector designed to target the R2 allele was exclusively integrated into the R2 allele in all the clones. Three rag-2$^{-/+}$ colonies identified above were used for embryonic cloning to generate 40-day fetuses as below.

Nuclear transfer was conducted according to the procedures in Cibelli, J. B. et al, *Science* 280:1256 (1998). Briefly, oocytes were matured in vitro, stripped of cumulus cells and enucleated at about 18 to 20 hours post maturation (hpm). At about 24 hpm, an individual rag-2$^{-/+}$ fibroblast was placed in the pervitelline space of a recipient oocyte and fused by electrofusion using a pulse of 120 volts for 15 µsec gap chamber. At around 26 hpm, activation of the NT unit was accomplished by a suitable procedure such as a 4-minute exposure to ionomycin (5 µM) in TL-HEPES supplemented with 1 mg/ml BSA and then washed for 5 minutes in TL-HEPES supplemented with 30 mg/ml BSA. Throughout the ionomycin treatment, NT units were also exposed to 2 mM DMAP. Following the wash, NT units were then transferred into a microdrop of culture medium containing 2 mM DMAP and cultured at 38.5° C. in 5% $CO_2$ for 4 or 5 hours. Alternatively, activation can be effected using cycloheximide and cytochalasin D procedure described infra. Embryos were washed and placed in medium plus 10% FCS and 6 mg/ml BSA in four well plates containing a confluent feeder layer of mouse embryonic fibroblasts. The NT units were then cultured for three additional days at 38.5° C. and 5% $CO_2$. Culture medium was changed every 3 days until 5 to 8 days after activation.

At 40 days of gestation, four fetuses were collected, all of which were confirmed to be the expected rag-2$^{-/+}$ genotype. One of them, cell line 279R, was subsequently used for the second round of gene targeting to generate homozygous rag-2$^{-/+}$ cell lines. Transfection was performed as described above, except that the pR3KOhyg was used to disrupt the remaining allele R3. Screening of the homozygous colonies were done as described above, except for using the following primer pair RKOhygF (5'-TTCCCAATACGAGGTCGC-CAACATCTTCTT-3'; SEQ ID NO: 5) and RKOhygR (5'-AATTCCTTTGGGTGTTAGCTTCTTTACTGGTT-3'; SEQ ID NO: 6). Out of 161 screened clones, about 30% of them generated the expected PCR products. As a result of sequencing of the PCR products, the KO vector designed to target R3 allele was exclusively integrated into the R3 allele in all the clones. Four rag-2$^{-/-}$ colonies identified above were used for embryonic cloning to generate 40-day fetuses and calves as described above.

The resulting rag-2 (−/−) bovines were viable. The rag-2 (−/−) bovines had the phenotype of wild-type bovines, with the exception of the symptoms of opportunistic infections (e.g., fever, fungal infections, and diarrhea). The rag-2 (−/−) bovines died of opportunistic infections at 6-7 weeks of age.

Figure 4:
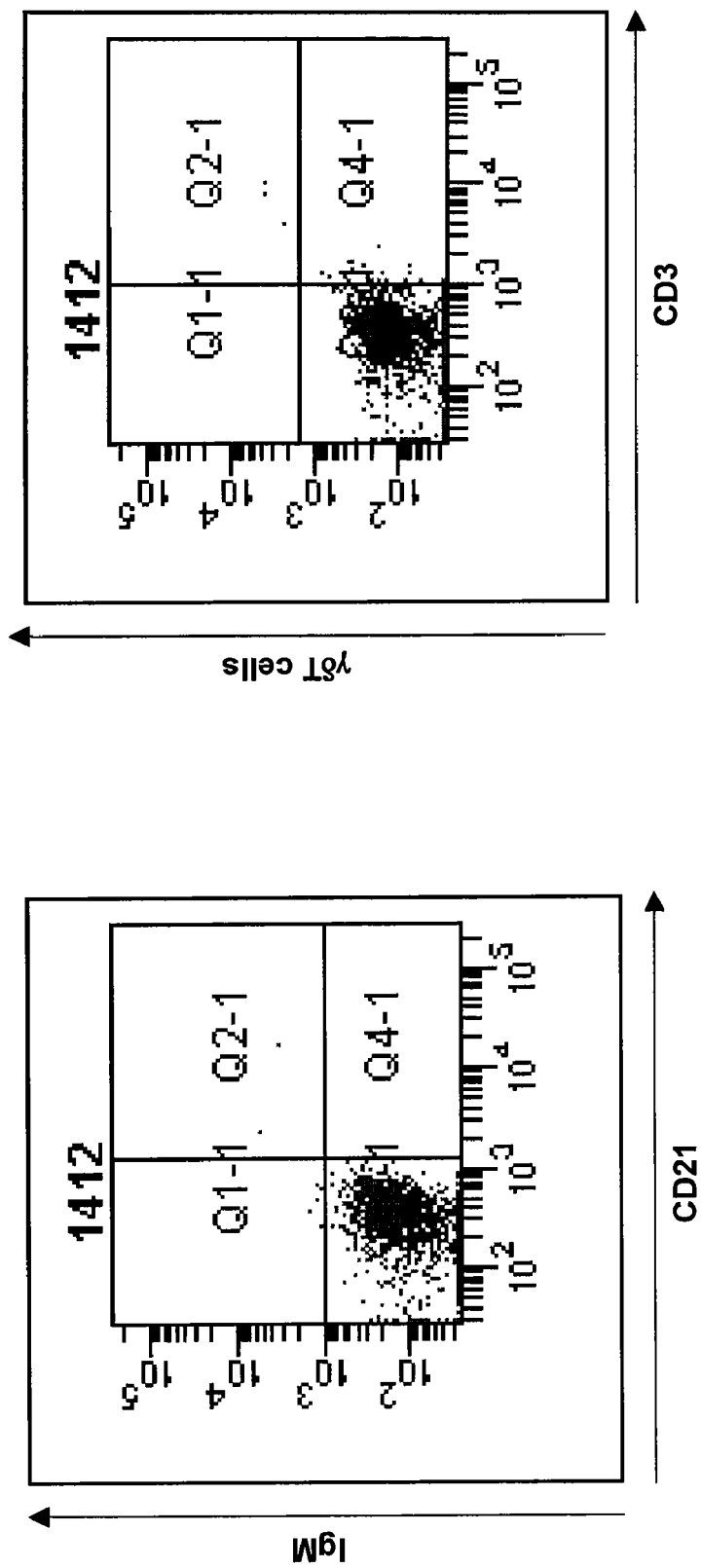
FIG. 4. This figure shows fluorescence-activated cell sorting (FACS) data of blood cells obtained from rag-2 (−/−) bovines stained with anti-IgM and anti-CD21 antibodies (left panel), or anti-CD3 and anti-γδ T-cell receptor antibodies (right panel).

In order to determine the loss of B- and T-cell production in rag-2 (−/−) bovines, peripheral blood was withdrawn from some of the above described rag-2 (−/−) bovines and labeled with B-cell- and T-cell-specific antibodies: anti-IgM and anti-CD21 antibodies, and anti-CD3 and anti-γδ T-cell receptor antibodies, respectively. The fluorescence of the resulting labeled blood cells was measured using FACS analysis. The data indicate that the rag-2 (−/−) bovines lacked viable B- and T-cells (FIG. 4).

Example 3

Transplantation of Human HSC-Enriched Cells into Rag-2 Knockout Bovine Fetuses

Populations of human cells enriched for human hematopoietic cells enriched for CD34$^+$ cells will be obtained by standard procedures. They will be introduced into the fetus using an ultrasound guided transvaginal injection method. One arm is inserted into the rectum and is used to manipulate the fetus. The peritoneal cavity of the fetus is located using the ultrasound probe inserted into the vagina. The vaginal probe is moved adjacent to the fetus and an injection needle is extended beyond the probe holder and into the fetus for cell injection. Alternatively, the umbilical cord is held in position by rectal palpation and the needle is inserted into the umbilical artery. The methods are similar to those used for collection of amniotic samples or for ovarian follicle aspirations.

Example 4

Demonstration of Exclusive Production of Polyclonal Human Ig in RAG-KO/Human HSC-Enriched Transplanted Bovines Blood obtained from RAG-KO/enriched-HSC transplanted calves will be subjected to species-specific ELISA to determine if the animals are producing exclusively human Ig or if some bovine Ig is produced. In addition, Ig will be precipitated from each serum sample by mixing with an equal volume of saturated ammonium sulfate. After collection, the precipitate will be dissolved in 5 ml or PBS (pH, 7.2) and dialyzed overnight. The dialyzate will be passed over a column of CNBr-Sepharose to which polyclonal rabbit anti-human Ig has been conjugated. After binding Ig from the serum, the column will be washed with 5 to 10 column volumes of PBS and then sequentially eluted with successive passages of 5 column volumes of following series of buffers: pH 7.0, 0.05 M sodium phosphate; pH 5.5, 0.05 M sodium citrate; pH 4.3, 0.5 M sodium acetate; pH 2.3, and 0.5 M glycine. Each of the fractions eluted will be checked by bovine and human Ig specific ELISA to verify the presence of human Ig and the absence of bovine Ig.

After its validation as human Ig by ELISA, each purified human Ig sample will be subjected to western blot analysis with class-specific anti-human Ig antibodies and isoelectric focusing. The western blot analysis will determine the range of different human Ig classes produced and isoelectric focusing will demonstrate that the antibody is polyclonal. With regard to human Ig class, the classes detected by western blotting will vary with the age of the animal. Newborns will likely show a predominance of human Ig, but older calves will be expected to produce various IgG subclasses and IgA, in addition to IgM.

Example 5

Demonstration that Immunization of RAG-KO/Enriched Calves Response to Immunization of Antigen-Specific Antibody At 60 days of age, RAG-KO/enriched-HSC calves are immunized with tetanus toxoid and the anti-tetanus toxin antibody titer is determined at weekly intervals for 4 weeks following immunization. ELISA using rabbit anti-human antibody as second step detecting reagents will be used to demonstrate that the anti-tetanus antibody response is human antibody. To confirm that the anti-tetanus response is comprised of exclusively human Ig, control experiments using anti-bovine antibody are performed in parallel.

What is claimed is:

1. A method for producing a cloned bovine, wherein the expression of both copies of the rag-2 gene have been knocked out and wherein said bovine lacks viable B- and T-cells, which comprises the following steps:
   (i) producing a donor bovine fibroblast cell or nucleus therefrom wherein the expression of one or both copies of the rag-2 gene has been eliminated by targeted disruption;
   (ii) fusing or inserting said donor fibroblast cell or nucleus into an enucleated bovine oocyte, to produce an embryo;
   (iii) introducing said embryo into a female bovine; and
   (iv) obtaining a cloned fetus or bovine animal that expresses the genotype of the donor fibroblast cell, in which the expression of one or both copies of the rag-2 gene has been eliminated; and
   (v) optionally, mating said bovine animal with another bovine animal wherein one copy of the rag-2 gene has been knocked out and selecting progeny wherein both copies of the rag-2 gene have been knocked out resulting in a lack of viable V-and T-cells in said bovine animal.

2. The method of claim 1, wherein said one or both copies of the rag-2 gene has been eliminated by targeted disruption with pR3KOhyg or pR2KObsr.

3. A method for producing a cloned bovine, wherein the expression of both copies of the rag-2 gene have been knocked out by a three-step process which comprises the following steps:
  (i) producing a donor bovine fibroblast an cell wherein the expression of one copy of the rag-2 gene has been eliminated by targeted disruption with a first DNA construct that provides for targeted disruption of said rag-2 gene;
  (ii) fusing or inserting said donor fibroblast cell or nucleus therefrom into an enucleated bovine oocyte to produce an embryo;
  (iii) contacting a fibroblast cell from said embryo with a second DNA construct under conditions that result in the elimination of the expression of the second copy of the rag-2 gene by homologous recombination; and
  (iv) fusing or inserting the resulting fibroblast cell or nucleus therefrom, in which both copies of the rag-2 gene have been knocked out, into an enucleated bovine oocyte or blastomere, to produce an embryo which does not express rag-2, resulting in a lack of viable B-and T-cells in said bovine animal.

4. The method of claim 3, wherein the first DNA construct is pR3KOhyg and the second DNA construct is pR2KObsr.

5. The method of claim 1, wherein the fibroblast cell of step (i) is produced by sequentially contacting said cell with two knockout constructs which in combination provide for knockout of both copies of the rag-2 gene.

6. The method of claim 5, wherein the said two knockout constructs comprise different selectable markers thereby providing for the selection of fibroblasts wherein both copies of the rag-2 gene are eliminated.

7. The method of claim 6, wherein the two knockout constructs are pR3KOhyg and pR2KObsr.

8. The method of claim 1, wherein both copies of the rag-2 gene have been eliminated in the embryo of step (ii).

9. A transgenic bovine wherein both copies of the rag-2 gene have been knocked out resulting in a lack of viable B-and T-cells in said bovine animal.

* * * * *

UNITED STATES PATENT AND TRADEMARK OFFICE
CERTIFICATE OF CORRECTION

| | | |
|---|---|---|
| PATENT NO. | : 7,820,878 B2 | Page 1 of 1 |
| APPLICATION NO. | : 12/151181 | |
| DATED | : October 26, 2010 | |
| INVENTOR(S) | : Goldsby et al. | |

It is certified that error appears in the above-identified patent and that said Letters Patent is hereby corrected as shown below:

Column 26, Line 64, replace "V-and" with --B- and--.

Column 27, Line 5, replace "producing a donor bovine fibroblast an cell" with --producing a donor bovine fibroblast cell--.

Column 28, Line 1, replace "B-and" with --B- and--;

Line 19, replace "B-and" with --B- and--.

Signed and Sealed this
Tenth Day of January, 2012

David J. Kappos
*Director of the United States Patent and Trademark Office*

SEQUENCE LISTING

<160> NUMBER OF SEQ ID NOS: 1

<210> SEQ ID NO 1
<211> LENGTH: 1456
<212> TYPE: DNA
<213> ORGANISM: Bovine

<400> SEQUENCE: 1

```
atgtcactac agatggtaac agtcggaaat agcatagcct taattcaacc aggcttctcg        60
ttaatgaatt ttgatgggca agttttcttc tttggccaaa aaggctggcc caagaggtct       120
tgccccactg gagttttcca ttttgaggta aagcataatc atcttaaact gaagcctgca       180
gttttctcta aggattcctg ctaccttcct cctcttcgat accgggccac ttgcacattc       240
agcggccaac ttggagtctg aaaagcatca gtacatcatc catggaggaa aaacaccaaa       300
caatgagctt tcagataaga tttatgtgat gtctgttgtt tccaagaaca acaaaaaagt       360
tacctttcgc tgcacagaga aggacttggt aggagacatt cctgaaggca gatatggtca       420
ttccattgat gtggtgtata gtcggggggaa aagtatgggt gttctctttg gaggacggtc       480
atacatacct tctgcccaaa gaaccacaga gaaatggaac agtgtagctg actgcctgcc       540
ccatgtcttc ttggtggatt ttgaatttgg gtgctctacg tcatacattc ttccagaact       600
tcaagatgga ctatctttc atgtctccat tgccagaaat gataccgttt atattttagg       660
aggccattca cttgccaata acatccgccc tgccaatctg tacagaataa gggttgatct       720
ccccctgggt agcccagctg tggagtgcac agtcttgcca ggaggaatct ctgtctccag       780
tgcaatcctg actcaaataa gcaatgatga atttgttatt gttggtggct atcagcttga       840
aaatcaaaaa agaatggtct gtaacatcat ctctttcaag tataacaaga tagacattct       900
tgagatggaa accccagatt ggaccccaga tattaagcac agcaagatat ggtttggaag       960
caacatggga aatggaactg ttttcctcgg cataccagga gacaataaac aggctgtttc      1020
agaagcattt tacttctata cattgaaatg tgctgaagac gatgtgaacg aagatcagat      1080
aactttgaca agtagtcaga catcaacaga agacccaggg gactccactc cctttgaaga      1140
ctcagaagaa ttttgcttca gcgcagaagc aaacagtttc gatggtgatg atgaatttga      1200
cacctacaat gaagatgatg aggaagatga gtctgagaca ggctattgga ttacatgctg      1260
ccctacttgt gatgtggata tcaatacgtg ggtaccattt tattcaactg agctcaacaa      1320
gcctgccatg atctattgct ctcatggaga tggacattgg gtccatgccc agtgtatgga      1380
tctggcagaa cgcaccacct catccatcta tcagaaggaa gcaataaata ttaytgtaac      1440
gagcatgtgg agatag                                                     1456
```